United States Patent
Bagci et al.

(10) Patent No.: US 10,157,462 B2
(45) Date of Patent: Dec. 18, 2018

(54) SYSTEM AND METHOD FOR IMAGE-BASED QUANTIFICATION OF WHITE AND BROWN ADIPOSE TISSUE AT THE WHOLE-BODY, ORGAN AND BODY-REGION LEVELS

(71) Applicant: University of Central Florida Research Foundation, Inc., Orlando, FL (US)

(72) Inventors: Ulas Bagci, Orlando, FL (US); Sarfaraz Hussein, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 57 days.

(21) Appl. No.: 15/634,797

(22) Filed: Jun. 27, 2017

(65) Prior Publication Data
US 2018/0165808 A1    Jun. 14, 2018

Related U.S. Application Data

(60) Provisional application No. 62/355,060, filed on Jun. 27, 2016.

(51) Int. Cl.
*G06K 9/00* (2006.01)
*A61B 6/00* (2006.01)
(Continued)

(52) U.S. Cl.
CPC .......... *G06T 7/0012* (2013.01); *A61B 6/032* (2013.01); *A61B 6/037* (2013.01); *A61B 6/50* (2013.01); *A61B 6/5217* (2013.01); *G06K 9/4604* (2013.01); *G06K 9/4638* (2013.01); *G06K 9/627* (2013.01); *G06K 9/6269* (2013.01); *G06T 7/00* (2013.01); *G06T 7/11* (2017.01); *G06K 2209/051* (2013.01); *G06T 2207/10081* (2013.01); *G06T 2207/10104* (2013.01);
(Continued)

(58) Field of Classification Search
USPC ........ 382/100, 103, 106, 128–134, 154–155, 382/162, 168, 173, 181, 190, 199, 214, 382/219, 220, 224, 254, 274, 276, 382/286–291, 312; 378/19, 21; 600/439; 424/158.1; 601/3
See application file for complete search history.

(56) References Cited

U.S. PATENT DOCUMENTS

| | | | |
|---|---|---|---|
| 2007/0053485 A1* | 3/2007 | Kobayashi | ........... A61B 5/4872 378/19 |
| 2011/0144545 A1* | 6/2011 | Fan | ......................... A61N 7/02 601/3 |

(Continued)

OTHER PUBLICATIONS

Tong, Y., et al. Optimization of abdominal fat quantification on CT imaging through use of standardized anatomic space: a novel approach. Medical physics, Jun. 2014; 41(6): 063501.
(Continued)

*Primary Examiner* — Seyed H Azarian
(74) *Attorney, Agent, or Firm* — Michele L. Lawson; Smith & Hopen, P.A.

(57) ABSTRACT

A system and method for automatically detecting and quantifying adiposity distribution is presented herein. The system detects, segments and quantifies white and brown fat adipose tissues at the whole-body, body region, and organ levels.

16 Claims, 7 Drawing Sheets

(51) Int. Cl.
| | | |
|---|---|---|
| A61N 7/02 | (2006.01) | |
| G06T 7/00 | (2017.01) | |
| A61B 6/03 | (2006.01) | |
| G06T 7/11 | (2017.01) | |
| G06K 9/46 | (2006.01) | |
| G06K 9/62 | (2006.01) | |

(52) U.S. Cl.
CPC .............. G06T 2207/10132 (2013.01); G06T 2207/30024 (2013.01)

(56) References Cited

U.S. PATENT DOCUMENTS

| | | | | |
|---|---|---|---|---|
| 2012/0157842 A1* | 6/2012 | Davis | ............... | A61N 7/02 600/439 |
| 2015/0366865 A1* | 12/2015 | Khan | ............... | A61K 31/48 424/158.1 |
| 2018/0009903 A1* | 1/2018 | Lijnen | ............... | C12Q 1/37 |

OTHER PUBLICATIONS

Muzik O., et al. 15O PET measurement of blood flow and oxygen consumption in cold-activated human brown fat. Journal of Nuclear Medicine, Apr. 2013; 54(4): 523-531.

Cohade, C., et al. Uptake in supraclavicular area fat ("USA-Fat"): description on 18F-FDG PET/CT. Journal of Nuclear Medicine, Feb. 2003; 44(2): 170-176.

Gilsanz, V., et al. Functional brown adipose tissue is related to muscle volume in children and adolescents. The Journal of Pediatrics, May 2011; 158(5): 722-726.

Zhao, B., et al. Automated quantification of body fat distribution on volumetric computed tomography. Journal of Computer Assisted Tomography, Sep. 2006; 30(5): 777-783.

Romero, D., et al. Quanification of subcutaneous and visceral adipose tissue using CT. In: Medical Measurement and Applications, 2006. MeMea 2006. IEEE International Workshop on pp. 128-133. IEEE.

Pednekar, A., et al. Automatic segmentation of abdominal fat from CT data. In: WACV 2005. vol. 1, pp. 308-315. IEEE.

Mensink S.D., et al. Development of automated quantification of visceral and subcutaneous adipose tissue volumes from abdominal CT scans. In: SPIE Medical Imaging, 2011. pp. 79632Q-79632Q. International Society for Optics and Photonics.

Kim, Y.J., et al. Body Fat Assessment Method Using CT Images with Separation Mask Algorithm, May 2012; Journal of Digital Imaging; 26(2): 155-162.

Chung, H., et al. Automated segmentation of muscle and adipose tissue on CT images for human body composition analysis. In: SPIE Medical Imaging, Mar. 2009; vol. 7261: 72610K-72610K International Society for Optics and Photonics.

Kim, Y.J., et al. Computerized Automated Quantification of Subcutaneous and Visceral Adipose Tissue from Computed Tomography Scans: Development and Validation Study, Feb. 2016; Journal of Medical Internet Research; Medical Informatics 4(1): e2.

Gifford, A. et al., Human brown adipose tissue depots automatically segmented by positron emission tomography/computed tomography and registered magnetic resonance images. Journal of Visualized Experiments, Feb. 2015; 96:e52415, pp. 1-12.

Shi et al., Robust separation of visceral and subcutaneous adipose tissues in micro-CT of mice, Jul. 2013, 35th Annual International Conference of IEEE EMBS, pp. 2312-2315.

Baba, S., et al. CT Hounsfield units of brown adipose tissue increase with activation: preclinical and clinical studies. Journal of Nuclear Medicine, Feb. 2010; 51(2): 246-250.

Cypess, A.M., Lehman, S., Williams, G., Tal, I., Rodman, D., Goldfine, A.B., Kuo, F.C., Palmer, E.L., Tseng, Y.H., Doria, A., Kolodny, G.M., Kahn, C.R.: Identification and Importance of Brown Adipose Tissue in Adult Humans. New England Journal of Medicine 360(15), 1509-1517 (2009).

Krizhevsky, A., Sutskever, I., Hinton, G.E.: Imagenet classification with Deep Convolutional Neural Networks. In: Advances in Neural Information Processing Systems. pp. 1097-1105 (2012).

Shin, H.C., Roth, H.R., Gao, M., Lu, L., Xu, Z., Nogues, I., Yao, J., Mollura, D., Summers, R.M.: Deep convolutional neural networks for computer-aided detection: CNN architectures, dataset characteristics and transfer learning. IEEE Transactions on Medical Imaging 35(5), 1285-1298 (2016).

Chatfield, K., Simonyan, K., Vedaldi, A., Zisserman, A.: Return of the devil in the details: Delving deep into convolutional nets. In: BMVC (2014).

Yoshizumi, T., Nakamura, T., Yamane, M., Waliul Islam, A.H.M., Menju, M., Yamasaki, K., Arai, T., Kotani, K., Funahashi, T., Yamashita, S., et al.: Abdominal fat: Standardized technique for measurement at ct 1. Radiology 211 (1), 283-286 (1999).

Udupa, J.K., Odhner, D., Zhao, L., Tong, Y., Matsumoto, M.M., Ciesielski, K.C., Falcao, A.X., Vaideeswaran, P., Ciesielski, V., Saboury, B., et al.: Body-wide hierarchical fuzzy modeling, recognition, and delineation of anatomy in medical images. Medical Image Analysis 18(5), 752-771 (2014).

Fischler, M.A., Bolles, R.C.: Random sample consensus: a paradigm for model fitting with applications to image analysis and automated cartography. Communications of the ACM 24(6), 381-395 (1981).

Sugiyama, M., Borgwardt, K.: Rapid distance-based outlier detection via sampling. In: Advances in Neural Information Processing Systems. pp. 467-475 (2013).

Bagci, U., Udupa, J.K., Mendhiratta, N., Foster, B., Xu, Z., Yao, J., Chen, X., Mollura, D.J.: Joint segmentation of anatomical and functional images: Applications in quantification of lesions from PET, PET-CT, MRI-PET, and MRI-PET-CT images. Medical Image Analysis 17(8), 929-945 (2013).

Criminisi, A., et al. Regression forests for efficient anatomy detection and localization in computed tomography scans. Medical image analysis, 17(8):1293-1303, 2013.

Chao Lu, Yefeng Zheng, Neil Birkbeck, Jingdan Zhang, Timo Kohlberger, Christian Teijien, Thomas Boetger, James S Duncan, and S Kevin Zhou. Precise segmentation of multiple organs in ct volumes using learning-based approach and information theory. In Medical Image Computing and Computer-Assisted Intervention— MICCAI 2012, pp. 462-469. Springer, 2012).

Yan, Zhennan, et al. Bodypart recognition using multi-stage deep learning. In Information Processing in Medical Imaging, pp. 449-461. Springer, 2015).

Prakash, K.B., Srour, H., Velan, S.S., Chuang, K.H: A method for the automatic segmentation of Brown Adipose Tissue. Magnetic Resonance Materials in Physics, Biology and Medicine 29(2), 287-299 (2016).

Flynn, A., Li, Q., Panagia, M., Abdelbaky, A., MacNabb, M., Samir, A., Cypess, A.M., Weyman, A.E., Tawakol, A., Scherrer-Crosbie, M.: Contrast-Enhanced Ultrasound: A Novel Noninvasive, Nonionizing Method for the Detection of Brown Adipose Tissue in Humans. Journal of the American Society of Echocardiography 28(10), 1247-1254 (2015).

Xu, Z. et al., Segmentation based denoising of PET images: An iterative approach via regional means and affinity propagation. International Conference on Medical Image Computing and Computer-Assisted Intervention, pp. 698-705. (2014).

Xu, Z., Bagci, U., Gao, M., Mollura, D.J.: Highly precise partial volume correction for PET images: An iterative approach via shape consistency. In: 2015 IEEE 12th International Symposium on Biomedical Imaging (ISBI), pp. 1196-1199. IEEE (2015).

Wang, H., Udupa, J.K., Odhner, D., Tong, Y., Zhao, L., Torigian, D.A.: Automatic anatomy recognition in whole-body PET/CT images. Medical Physics 43(1), 613-629 (2016).

* cited by examiner

Figure 1A-C

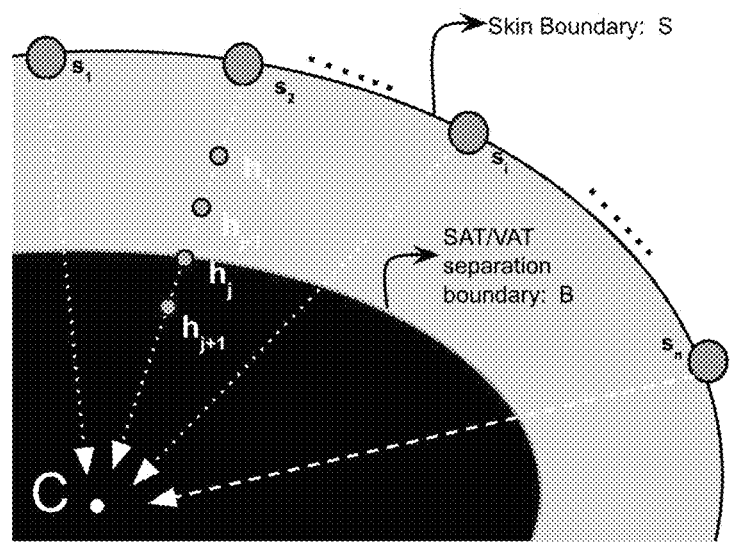
Figure 4
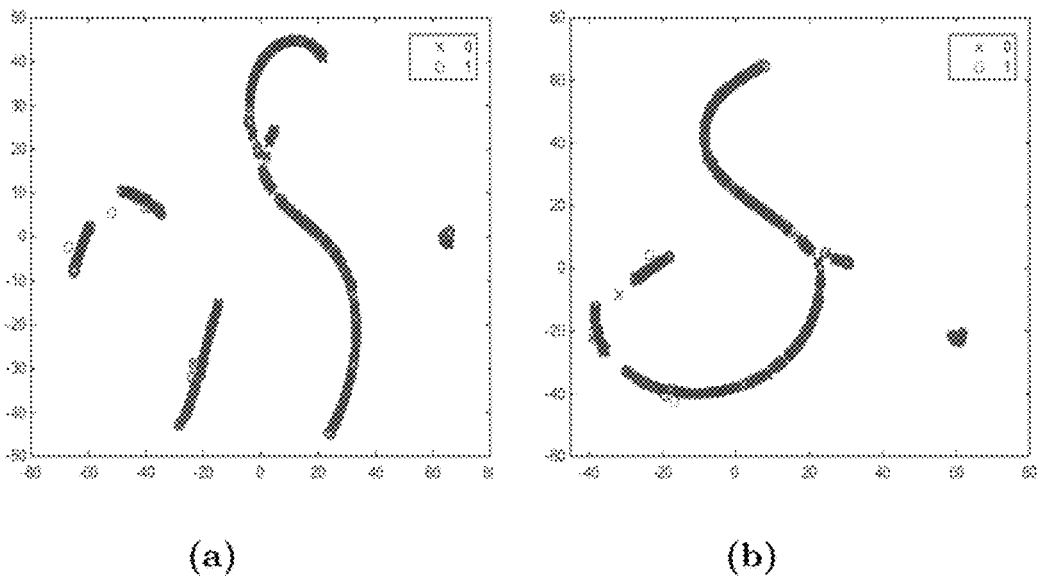
(a)           (b)
Figure 5A-B

Figure 8A-G

SYSTEM AND METHOD FOR IMAGE-BASED QUANTIFICATION OF WHITE AND BROWN ADIPOSE TISSUE AT THE WHOLE-BODY, ORGAN AND BODY-REGION LEVELS

CROSS REFERENCE TO RELATED APPLICATIONS

This application claims priority to U.S. Provisional Application No. 62/355,060 entitled "System and Method For Image-Based Quantification of White and Brown Adipose Tissue at the Whole-Body. Organ and Body-Region Levels", filed Jun. 27, 2016, the contents of which are hereby incorporated by reference into this disclosure.

FIELD OF INVENTION

This invention relates to methods of quantifying abdominal obesity. Specifically, the invention describes a system and method of quantifying white and brown adipose tissue from PET/CT scans using a novel computer-aided detection algorithm at the tissue, organ and body region levels.

BACKGROUND OF THE INVENTION

Obesity is one of the most prevalent health conditions with about 30% of the world's and over 70% of the United States' adult population being either overweight or obese, causing an increased risk for cardiovascular diseases, diabetes, and certain types of cancer. (Ng, M., Fleming, T., Robinson, M., Thomson, B., Graetz, N., Margono, C., Mullany, E. C., Biryukov, S., Abbafati, C., Abera, S. F., et al.: Global, regional, and national prevalence of overweight and obesity in children and adults during 1980-2013: a systematic analysis for the global burden of disease study 2013. The Lancet 384(9945), 766-781 (2014)) Central obesity, also known as abdominal obesity, is the excessive build-up of fat around stomach and abdomen. Central obesity has been held responsible for high levels of LDL cholesterol and triglycerides and lower levels of HDL cholesterol. There is a correlation between central obesity and disorders such as cardiovascular disease, heart attacks, strokes, high blood pressure, cancer, diabetes, osteoarthritis, fatty liver disease, metabolic syndrome and depression.

A simple method of assessing abdominal obesity is the waist circumference measurement. Generally, a waist circumference measurement above 88 cm for women and above 102 cm for men indicates abdominal obesity. However, this method does not take into account several important variables which should be considered such as the type of fat as well as the location of the abdominal fat. In addition, this method is more prone to errors in measurement and thus inaccuracies.

Another way to assess abdominal obesity is using a waist to hip ratio in which the waist measurement is divided by the hip measurement. The chance of a heart attack or stroke steadily increases as the ratio rises above 0.95 in men and 0.85 in women. Similar to only waist circumference measurements, this method is prone to errors in measurements which lead to inaccuracies.

Traditionally, Body Mass Index (BMI) has been used as a measure of obesity and metabolic health. BMI is the body mass (weight) divided by the square of the body height and is expressed in units of $kg/m^2$. Generally accepted ranges include: under 18.5 $kg/m^2$=underweight; 18.5 to 25 $kg/m^2$=normal; 25 to 30 $kg/m^2$=overweight; and over 30 $kg/m^2$=obese. One problem with BMI measurement is that it remains inconsistent across subjects, especially for underweight, obese and highly muscular individuals. BMI also reflects only total body fat without regard to fat distribution.

Volumetry of abdominal fat is considered a reliable, accurate, and consistent measure of body fat distribution. Because visceral adipose tissue (VAT) manifests itself mainly in abdominal region, it is considered an important marker for evaluating central obesity thus making quantification of VAT vital for precise diagnosis and timely treatment of numerous diseases such as heart attacks, diabetes and cancer. VAT drains directly through portal circulation directly into the liver. VAT releases several bioactive molecules and hormones, such as adiponectin, leptin, tumour necrosis factor, resistin and interleukin 6 (IL-6) which are related to elevated glucose levels, hypertension, cardiovascular disease and other malignancies. In clinical literature, the association between VAT and different diseases has been thoroughly discussed. For instance, visceral obesity quantified through Computed Tomography (CT) was found to be a significant risk factor for prostate cancer. (Von Hafe, P., Pina, F., Pérez, A., Tavares, M., Barros, H.: Visceral Fat Accumulation as a Risk Factor for Prostate Cancer. Obesity 12(12), 1930 (2004)). Visceral adiposity has been found to be a significant predictor of disease-free survival rate in resectable colorectal cancer patients. (Moon, H. G., Ju, Y. T., Jeong, C. Y., Jung, E. J., Lee, Y. J., Hong, S. C., Ha, W. S., Park, S. T., Choi, S. K.: Visceral Obesity may affect Oncologic Out-come in patients with Colorectal Cancer. Annals of Surgical Oncology 15(7), 1918-1922 (2008)). In contrast to Subcutaneous Adipose Tissue (SAT), VAT was concluded to have an association with incident cardiovascular disease and cancer after adjustment for clinical risk factors and general obesity. (Britton, K. A., Massaro, J. M., Murabito, J. M., Kreger, B. E., Hoffmann, U., Fox, C. S.: Body Fat Distribution, Incident Cardiovascular Disease, Cancer, and All-Cause Mortality. Journal of the American College of Cardiology 62(10), 921-925 (2013)). Speliotes et al. found VAT as the strongest correlate of fatty liver among all the other factors used in their study. (Speliotes, E. K., Massaro, J. M., Hoffmann, U., Vasan, R. S., Meigs, J. B., Sahani, D. V., Hirschhorn, J. N., O'Donnell, C. J., Fox, C. S.: Fatty liver is associated with dyslipidemia and dysglycemia independent of visceral fat: the Framingham Heart Study. Hepatology 51(6), 1979-1987 (2010)). VAT was found to be an independent predictor of all-cause mortality in men after adjustment for abdominal subcutaneous and liver fat. (Kuk, J. L., Katzmarzyk, P. T., Nichaman, M. Z., Church, T. S., Blair, S. N., Ross, R.: Visceral fat is an independent predictor of all-cause mortality in men. Obesity 14(2), 336-341 (2006)). All these clinical evidences show that the robust and accurate quantification of VAT can help improve identification of risk factors, prognosis, and long-term health outcomes.

Subcutaneous adipose tissue (SAT), on the other hand, does not seem to be associated with increases in risk factors for the same diseases associated with higher VAT. In fact, some studies have observed a potential beneficial role for SAT noting that subjects having increased hip and thigh fat mass have lower glucose and lipid levels independent of abdominal fat. (Porter, S. A. et al., Abdominal subcutaneous adipose tissue: a protective fat depot?, *Diabetes Care*, 2009, 32(6): 1068-1075).

Unfortunately, it is difficult to automatically separate VAT from subcutaneous adipose tissue (SAT) because both VAT and SAT regions share similar intensity characteristics, similar Hounsfield unit (HU) in computerized tomography (CT), and are vastly connected. (FIG. 1B) Currently, to segregate these two fat types, radiologists usually use different morphological operations as well as manual interactions, however this process is subjective and not attractive in routine evaluations. Therefore, a set of representative slices at the umbilical level are often used for quantifying central obesity. (Tong, Y., Udupa, J. K., Torigian, D. A.: Optimization of abdominal fat quantification on CT imaging through use of standardized anatomic space: A novel approach. Medical physics 41(6), 063501 (2014)). However, these selections do not infer volumetric quantification. As such, inefficient and inaccurate quantification remains a major problem in clinical evaluation of central obesity and body fat distribution.

Brown adipose tissue (BAT), commonly known as a brown fat, and white adipose tissue (WAT) are two types of adipose tissue found in mammals. (FIG. 1A) Quantification of white adipose tissue and its subtypes is an important task in clinical evaluation of several conditions such as obesity, cardiac diseases, diabetes and other metabolic syndromes. BAT quantification studies are mostly based on qualitative observation of expert radiologists and nuclear medicine physicians since there is no automated CAD system available for this purpose. In those studies, after strictly chosen specific anatomical locations are explored for BAT presence, the quantification process is conducted either by manual or semi-automated delineation methods. (Muzik, O., Mangner, T. J., Leonard, W. R., Kumar, A., Janisse, J., Granneman, J. G.: 15o pet measurement of blood flow and oxygen consumption in cold-activated human brown fat. Journal of Nuclear Medicine 54(4), 523-531 (2013); Cohade, C., Osman, M., Pannu, H., Wahl, R.: Uptake in supraclavicular area fat ("usa-fat"): description on 18f-fdg pet/ct. Journal of Nuclear Medicine 44(2), 170-176 (2003))

It was recently found that there is an inverse relationship between BAT activity and body fatness which may suggest that BAT is protective against body fat accumulation because of its energy dissipating activity thus making BAT a potential target for combating human obesity and related metabolic disorders. (Saito, M., Brown adipose tissue as a therapeutic target for human obesity, *Obesity Research & Clinical Practice,* 2013, Vol. 7, Issue 6, pp. e432-e438).

Since PET images have high contrast, thresholding and/or clustering based methods are well suited for delineation of uptake regions. Simple thresholding is used for segmenting the uptake region pertaining to the BATs for extracting metabolic BAT volume and standardized uptake value (SUV) based metrics. BAT is considered present if there are areas of tissue that are more than 5 mm in diameter; there is a CT density of between −190 to −30 Hounsfield Units (HU); and there is an SUV of 18F-FDG of at least 2. Region of interests (ROIs) are used to manually remove false positive (FP) regions from consideration. There may be further manual FP removal steps for differentiating uptake between BAT regions and lymph nodes, vessels, bones, and the thyroid. (Gilsanz, V., Chung, S. A., Jackson, H., Dorey, F. J., Hu, H. H.: Functional Brown Adipose Tissue is Related to Muscle Volume in Children and Adolescents. The Journal of pediatrics pp. 722-726 (2011)) Each of these manual identifications require extensive user knowledge of the anatomy and hence are prone to errors. Furthermore, in case of existence of pathologies, segregating pathologies from normal variants of 18F-FDG or BAT regions can be extremely challenging.

BATs are important for thermogenesis, and are considered as natural defense against hypothermia and obesity. (Cypess, A. M., Lehman, S., Williams, G., Tal, I., Rodman, D., Goldfine, A. B., Kuo, F. C., Palmer, E. L., Tseng, Y. H., Doria, A., Kolodny, G. M., Kahn, C. R.: Identification and importance of brown adipose tissue in adult humans. New England Journal of Medicine 360(15), 1509-1517 (2009)) In contrast to WAT, BATs are metabolically active, so functional imaging modalities can help in detecting these tissues. In this regard, sensitivity of Positron Emission Tomography (PET) imaging is much higher than that of magnetic resonance imaging (MRI) and computed tomography (CT) for visualizing and quantifying BATs. (FIG. 1C) However, PET lacks specificity due to limited structural information. When combined with CT and/or MRI, both specificity and sensitivity are increased due to incorporation of anatomical sites into the evaluation framework. Despite rapid improvements in the imaging facets of BAT detection, the available methods are limited to manual and semi-automated strategies; hence, they are time-consuming and non-reproducible.

Previous Work

Body fat quantification has been a long-time active area of research for medical imaging scientists. For abdominal fat (central obesity) quantification, Zhao et al. used intensity profile along the radii connecting sparse points on the outer wall (skin boundary) starting from the abdominal body center. (Zhao, B., Colville, J., Kalaigian, J., Curran, S., Jiang, L., Kijewski, P., Schwartz, L. H.: Automated quantification of body fat distribution on volumetric computed tomography. Journal of computer assisted tomography 30(5), 777-783 (2006)) Boundary contour is then refined by a smoothness constraint to separate VAT from SAT. This method, however, does not adapt to obese patients easily where the neighboring subcutaneous and/or visceral fat cavities lead to leakage in segmentation.

In another study, Romero et al. developed different search strategies based on heuristics to generate the abdominal wall mask on a small set of representative slices. However, this method is prone to inefficiencies for subjects in which the abdominal wall is too sparse. (Romero, D., Ramirez, J. C., M'armol, A.: Quantification of subcutaneous and visceral adipose tissue using ct. In: Medical Measurement and Applications, 2006. MeMea 2006. IEEE International Workshop on. pp. 128-133. IEEE (2006))

In a similar fashion, Pednekar describes a method based on a hierarchical fuzzy affinity function derived semi-supervised segmentation. As the method uses about half of its experimental data for training, its success was vague and dependent on the selection of training subjects especially when patient specific quantification is considered. (Pednekar, A., Bandekar, A. N., Kakadiaris, I., Naghavi, M., et al.: Automatic segmentation of abdominal fat from ct data. In: WACV 2005. vol. 1, pp. 308-315. IEEE (2005))

Mensink et al. proposed a series of morphological operations, however fine tuning of the algorithm was difficult for patient specific quantification, and this fine tuning would have to be repeated almost for every patient when the abdominal wall is too thin. (Mensink, S. D., Spliethoff, J. W., Belder, R., Klaase, J. M., Bezooijen, R., Slump, C. H.: Development of automated quantification of visceral and subcutaneous adipose tissue volumes from abdominal ct scans. In: SPIE Medical Imaging. pp. 79632Q-79632Q. International Society for Optics and Photonics (2011))

More recently, Kim et al. generated subcutaneous fat mask using a modified "AND" operation on four different directed masks with some success shown. However, logical and morphological operations make the whole quantification system vulnerable to inefficiencies. (Kim, Y. J., Lee, S. H., Kim, T. Y., Park, J. Y., Choi, S. H., Kim, K. G.: Body fat assessment method using ct images with separation mask algorithm. Journal of digital imaging 26(2), 155-162 (2013))

A more advanced method was presented by Chung in which SAT, VAT and muscle are separated using a joint shape and appearance model, however the reproducibility of the method is highly dependent on the model at hand. (Chung, H., Cobzas, D., Birdsell, L., Lieffers, J., Baracos, V. Automated segmentation of muscle and adipose tissue on ct images for human body composition analysis. In: SPIE Medical Imaging. pp. 72610K-72610K. International Society for Optics and Photonics (2009))

Based on a similar idea as in Zhou, a recent method by Kim et al. estimated the muscle boundary using a convex-hull and then performed smoothing by selecting points that minimize the distance between the contour and the organ regions. However, the performance is dependent on the goodness of fit of the convex-hull. Although the method addresses SAT-VAT separation at a volumetric level, it lacks the use of important appearance features and volumetric smoothing. (Kim, Y. J., Park, J. W., Kim, J. W., Park, C. S., Gonzalez, J. P. S., Lee, S. H., Kim, K. G., Oh, J. H.: Computerized Automated Quantification of Subcutaneous and Visceral Adipose Tissue From Computed Tomography Scans: Development and Validation Study. Journal of Medical Internet Research; Medical Informatics 4(1) (2016))

Recently, work has been done by Gifford et al. in which PET/CT scans are used to automatically generate a BAT mask, which is then applied to co-registered MRI scans of the patient thus enabling measurement of quantitative MRI properties of BAT without manual segmentation. (Gifford, A. et al., Human brown adipose tissue depots automatically segmented by positron emission tomography/computed tomography and registered magnetic resonance images, 2015, *Journal of Visualized Experiments*, 96:e52415) This approach differs from the approach described herein by the use of both PET/CT and MRI which requires four imaging visits from the patient. Similar to all other approaches, BAT masks were generated by using SUV and HU information jointly such that fat regions are defined manually in CT images and this step is followed by checking the SUV's of corresponding pixels in PET images, if higher values are observed, BAT is considered for that pixel. Unfortunately, this procedure does not optimize the BAT region definition as it only includes sub-optimal thresholding and does not access the existence of abnormalities in contrast to the approach described herein.

Shi et al. describe a robust two-stage VAT/SAT separation framework for CT data in which adipose tissue is distinguished from other tissue types through a robust mixture of Gaussian model after which spatial recognition relevant to anatomical locations is used to differentiate between visceral and subcutaneous adipose tissue. (Shi et al., Robust separation of visceral and subcutaneous adipose tissues in micro-CT of mice, 2013, 35$^{th}$ *Annual International Conference of IEEE EMBS, pp.* 2312-2315) The Shi et al. approach has the disadvantage of being tested only on small animal images where internal organs are visualized with better spatial resolution, and parameters of the methods are easier to tune. In the low-resolution, non-contrast CT images, that are used for human cases, it is extremely difficult to set parameters. Shi et al. does not provide any evidence of being used in human CT scans and the approach would likely not be successful in humans since the approach is not data-driven and thus cannot account for personalized differences such as anatomical variations (different BMIs, etc.) or pathology presence (tumors, bone cracks, etc.). In contrast, the approach described herein is data-driven, easily adjusting for different personalized parameters of each patient.

There has not been an automated Computer-Aided Detection (CAD) system proposed for BAT quantification using radiology scans. Existing studies are mostly based on the qualitative observations of expert radiologists and nuclear medicine physicians. In those studies, strictly chosen specific anatomical locations were explored for BAT presence. (Muzik, O., Mangner, T. J., Leonard, W. R., Kumar, A., Janisse, J., Granneman, J. G.: 15 O PET Measurement of Blood Flow and Oxygen Consumption in Cold-Activated Human Brown Fat. Journal of Nuclear Medicine 54(4), 523-531 (2013); Cohade, C., Osman, M., Pannu, H., Wahl, R.: Uptake in supraclavicular area fat ("USA-Fat"): Description on $^{18}$ F-FDG PET/CT. Journal of Nuclear Medicine 44(2), 170-176 (2003)). The quantification process was conducted either by manual or semi-automated delineation methods. Since PET images have high contrast, thresholding and clustering-based methods are well-suited for the delineation of uptake regions. Therefore, a simple thresholding was often used for segmenting uptake regions pertaining to BAT, allowing the extraction of volumetric and S U V (i.e., "standardized uptake value") based metrics. BAT is considered present if there are areas of tissues that are (i) more than 5 mm in diameter, (ii) CT density is restricted to −190 to −30 Hounsfield Units (HU), and (iii) have an SUV of 18F-fluorodeoxyglucose ($^{18}$F-FDG) of at least 2 g/ml in corresponding PET images. Here it is important to note that in Baba, the authors chose the thresholding value for SU $V_{max}$>3 g/ml to identify BAT regions. (Baba, S., Jacene, H. A., Engles, J. M., Honda, H., Wahl, R. L.: CT Hounsfield Units of Brown Adipose Tissue Increase with Activation: Preclinical and Clinical Studies. Journal of Nuclear Medicine 51(2), 246-250 (2010)). Hence, there is no clear consensus on the choice of SUV for BAT regions. In the last step, regions of interest (ROIs) are manually defined to remove false positive (FP) regions from consideration. Several manual FP removal steps may be required for differentiating uptake between BAT regions and lymph nodes, vessels, bones, and the thyroid. (Gilsanz, V., Chung, S. A., Jackson, H., Dorey, F. J., Hu, H. H.: Functional Brown Adipose Tissue is Related to Muscle Volume in Children and Adolescents. The Journal of Pediatrics pp. 722-726 (2011)). All these manual identifications require extensive user knowledge of the anatomy. Furthermore, in cases where pathologies are present, segregating pathologies from normal variants of $^{18}$F-FDG on BAT regions can be extremely challenging. (Cypess, A. M., Lehman, S., Williams, G., Tal, I., Rodman, D., Goldfine, A. B., Kuo, F. C., Palmer, E. L., Tseng, Y. H., Doria, A., Kolodny, G. M., Kahn, C. R.: Identification and Importance of Brown Adipose Tissue in Adult Humans. New England Journal of Medicine 360(15), 1509-1517 (2009)).

In light of the shortcomings of the current approaches, what is needed is a way to automate the detection, segmentation and quantification of SAT, VAT and BAT regions.

SUMMARY OF INVENTION

The inventors have developed a method for the automatic detection of white and brown adipose tissues using Positron Emission Tomography/Computed Tomography (PET/CT) scans as well as developed method for the quantification of these tissues at the whole-body and body-region levels. In general, the system and method are comprised of automatic body region detection using algorithms followed by SAT-VAT segmentation and BAT quantification and segmentation. Once the body region is detected, specific organs containing adipose tissue can be isolated and fat composition quantified by transferring 3D CNN features from a known non-medical source dataset to a medical imaging scan using Geodesic Flow Kernel.

The inventors propose a patient-specific automatic adiposity analysis system in which white adipose tissue (WAT) and its two sub-types, Visceral Adipose Tissue (VAT) and Subcutaneous Adipose Tissue (SAT), are first detected from CT scans. This process relies conventionally on manual or semi-automated segmentation, leading to inefficient solutions. The novel framework addresses this challenge by proposing an unsupervised learning method to separate VAT from SAT in the abdominal region for the clinical quantification of central obesity. This step is followed by a context driven label fusion algorithm through sparse 3D Conditional Random Fields (CRF) for volumetric adiposity analysis.

After detection of WAT from the scans, brown adipose tissue (BAT) is automatically detected, segmented, and quantified using PET scans because unlike WAT, BAT is metabolically active. After identifying BAT regions using PET, the inventors perform a co-segmentation procedure utilizing asymmetric complementary information from PET and CT. Finally, the inventors present a new probabilistic distance metric for differentiating BAT from non-BAT regions. The processes are integrated via an automatic body-region detection unit based on one-shot learning. Experimental evaluations conducted on 151 PET/CT scans achieve state-of-the-art performances in both central obesity as well as brown adiposity quantification.

The proposed computerized automatic detection (CAD) system is the first fully automated method for detecting, segmenting, and quantifying SAT, VAT and BAT regions from PET/CT scans. The proposed method for SAT-VAT segmentation and quantification is a multi-step method that starts with a novel automated abdominal and thorax region detection algorithm, based on deep learning features which differentiates between the two regions. The steps of the method include: (1) segmentation of Total Adipose Tissue (TAT) at the abdominal level; (2) estimation of initial boundary between SAT and VAT; (3) boundary refinement using an unsupervised learning method for separating VAT from SAT using appearance (via Local Outlier Scores) and geometric (via Median Absolute Derivation) cues; and (4) volumetric quantification of precise SAT-VAT separation based on integrated contextual information via a sparse 3D Conditional Random Fields (CRF) based label fusion algorithm. This work can be considered the largest central obesity quantification study (151 CT scans) to date, validating accurate region and abdominal fat detection algorithms.

For BAT detection and segmentation, preliminarily, canonical random forests are utilized with structure cues for automatic body region detection which allows the algorithm to be constrained to only potential BAT regions (head/neck and thorax). In step 1, the inventors first use a fixed HU interval to identify total adipose tissue (TAT) from CT images. In step 2, a seed sampling scheme was devised for extracting foreground and background cues from high uptake regions of PET images in head-neck and thorax regions only. The identified seeds are propagated into the corresponding CT scans as well using one-to-one correspondence with PET images to create PET-CT co-segmentation using Random Walk. In step 3, a PET-guided image co-segmentation algorithm is initiated on the hyper-graph (PET/CT) to delineate potential BAT regions. In step 4, a new probabilistic metric combining total variation and Cramer-Von Mises distances is used to differentiate BAT regions from non-BAT regions as a false positive rejection step. FIG. 2 shows the overview of the proposed system.

Organ detection is one of the most challenging problems lying at the confluence of medical imaging and supervised learning. As the deep learning based strategies are gaining popularity for classification and regression problems, organ detection in 3D Computed Tomography (CT) sequences experienced a diversification in advanced methods despite the scarcity of labeled medical data. To address the lack of labeled data, the transferability of 3D Convolutional Neural Networks (CNN) features learned from non-medical datasets onto the medical imaging domain was studied. It was found that the features learned from the non-medical dataset are deemed useful for organ detection problem as a moderately high level of detection rate was obtained. Specifically, the proposed method is based on Geodesic Flow Kernel (GFK) where transferring information from the source (action recognition dataset) into the target (CT organ detection) increases the default detection rate when only conventional deep learning strategies are used.

In one embodiment, a method of automatically detecting and quantifying white and brown adipose tissue from an imaging scan of a subject is presented comprising: providing the imaging scan of the subject; automatically detecting a body region of the subject in the imaging scan; separating and segmenting subcutaneous adipose tissue (SAT) from visceral adipose tissue (VAT) in the imaging scan of the subject; and detecting and segmenting brown adipose tissue (BAT) from other tissue in the imaging scan of the subject.

The body region detected can be an abdominal region or a thorax region that is automatically detected by using a detection algorithm based on deep learning features.

Separating and segmenting SAT from VAT is further comprised of the steps of: segmenting total adipose tissue (TAT) in the imaging scan; estimating an initial boundary between SAT and VAT in the abdominal region; removing outliers from the boundary; and fusing labels of boundary candidates across different slices and creating a fine SAT-VAT separating surface.

The outliers can be removed from the boundary using geometric median absolute derivation (MAD) and local outlier scores (LoOS). The SAT-VAT separating surface can be created using 3D Conditional Random Fields (CRF) using shape, anatomy and appearance cues.

Detecting and segmenting BAT is further comprised of: identifying total adipose tissue (TAT) in the imaging scan; performing automatic seed selection for BAT; delineating potential BAT regions; and differentiating BAT regions from non-BAT regions.

Fixed Hounsfield unit (HU) interval filtering can be used to identify TAT. Background and foreground seeds can be identified during automatic seed selection. Image co-segmentation using Random Walk (RW) can be used to delineate potential BAT regions. A probabilistic metric based on a combination of total variation and Cramer-Von Mises distances can be used to differentiate BAT regions from non-BAT regions.

The method can be further comprised of automatically detecting specific organs containing adipose tissue by: extracting 3D convolutional neural network (CNN) features from source data; transforming 3D CNN features from source data to target data by applying Geodesic Flow Kernal (GFK) to the 3D CNN features; and localizing the organ in a bounding volume using Random Forest wherein the target data is organ detection in 3D CT scans.

The imaging scan can be selected from the group consisting of a positron emission tomography/computed tomography (PET/CT) scan, a positron emission tomography/ magnetic resonance imaging scan (PET/MRI) and a contrast-enhanced ultrasound (CEUS) scan.

In another embodiment, a method of creating a risk profile of a subject by automatically detecting and quantifying white and brown adipose tissue from an imaging scan of the subject is presented comprising: providing the imaging scan of the subject; automatically detecting a body region of the subject in the imaging scan wherein the body region detected is an abdominal region or a thorax region; separating and segmenting subcutaneous adipose tissue (SAT) from visceral adipose tissue (VAT) in the imaging scan of the subject; detecting and segmenting brown adipose tissue (BAT) from other tissue in the imaging scan of the subject; and creating a risk profile based on the quantitative amount of VAT and BAT found in the subject.

Separating and segmenting subcutaneous adipose tissue (SAT) from visceral adipose tissue (VAT) in the imaging scan can be comprised of: automatically detecting white adipose tissue (WAT) in the imaging scan; segmenting total adipose tissue (TAT); estimating a SAT-VAT separation boundary; removing outliers using geometric median absolute derivation (MAD) and local outlier scores (LoOS); and fusing labels of boundary candidates across different slices of an image volume to create a fine SAT-VAT separating surface using 3D Conditional Random Fields (CRF) using shape, anatomy and appearance cues.

Detecting and segmenting brown adipose tissue (BAT) from other tissue can be comprised of: identifying TAT in the imaging scan; performing automatic seed selection for BAT; performing image co-segmentation; and differentiating BAT regions from non-BAT regions.

The method can be further comprised of automatically detecting specific organs containing adipose tissue by: extracting 3D convolutional neural network (CNN) features from source data; transforming 3D CNN features from source data to target data by applying Geodesic Flow Kernal (GFK) to the 3D CNN features; and localizing the organ in a bounding volume using Random Forest wherein the target data is organ detection in 3D CT scans.

The imaging scan can be selected from the group consisting of a positron emission tomography/computed tomography (PET/CT) scan, a positron emission tomography/ magnetic resonance imaging scan (PET/MRI) and a contrast-enhanced ultrasound (CEUS) scan.

BRIEF DESCRIPTION OF THE DRAWINGS

For a fuller understanding of the invention, reference should be made to the following detailed description, taken in connection with the accompanying drawings, in which:

FIG. 4 is an image depicting an illustration of skin boundary and hypothesis points along the radii connecting S with its centroid C. For each point in S, a set of hypotheses is generated which is along the line connecting the skin boundary point with the centroid C.

FIG. 5A-B is an image depicting t-SNE visualizations using (a) Euclidean and (b) Normalized Correlation distances. Better separation of classes can be clearly seen in (b).

DETAILED DESCRIPTION OF THE PREFERRED EMBODIMENT

Figure 1:
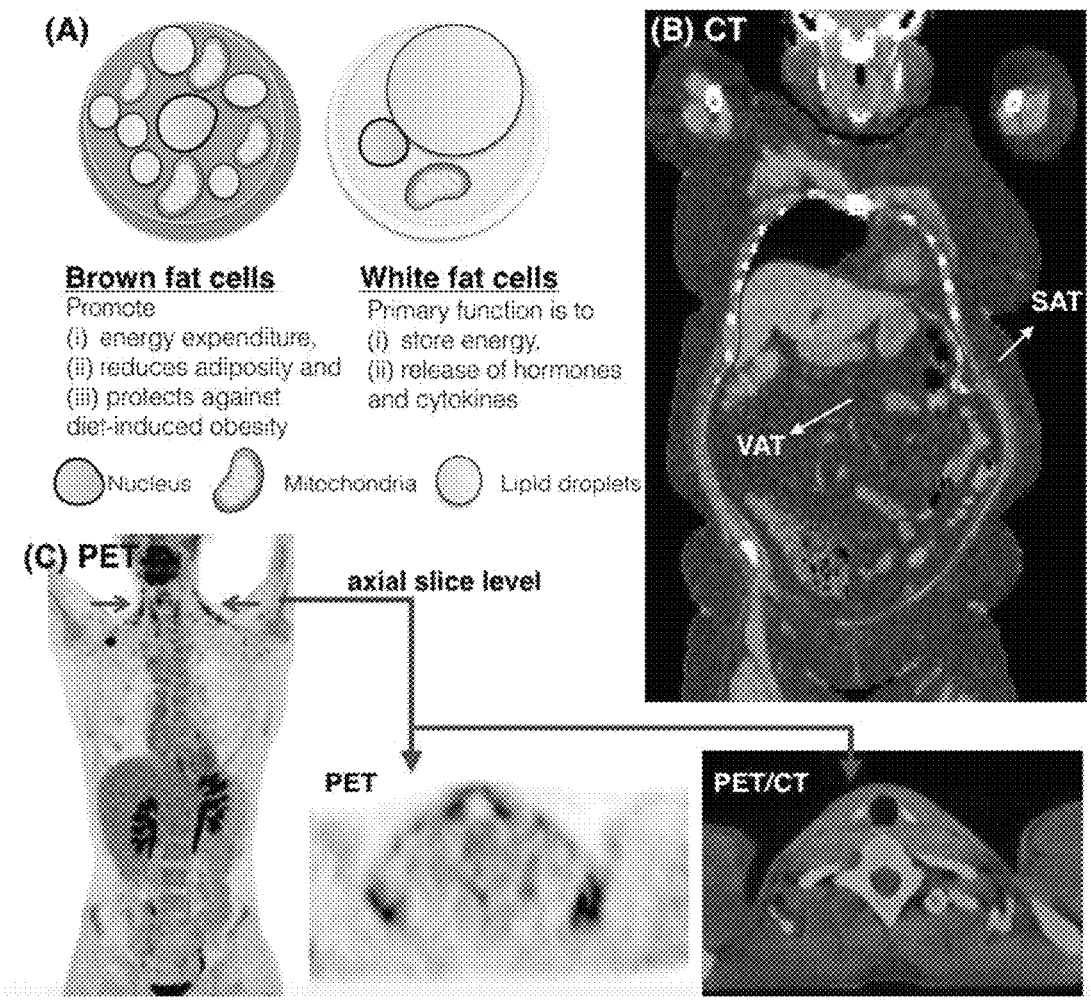
FIGS. 1A-C are a series of images depicting different types of adipose tissues in Positron Emission Tomography (PET) and Computed Tomography (CT) scans. (A) signifies the difference at cellular level between Brown Adipose Tissue (BAT) and White Adipose Tissue (WAT). In contrast to WAT, BAT is metabolically active and consumes energy. (B) shows Subcutaneous Adipose Tissue (SAT) and Visceral Adipose Tissue (VAT) in a coronal view of CT. The red boundary illustrates the thin muscular wall separating these two sub-types. The wall remains mostly discontinuous, making SAT-VAT separation significantly challenging. (C) depicts metabolically active BAT in PET (left/middle) and PET/CT fusion (right).
Figure 2:
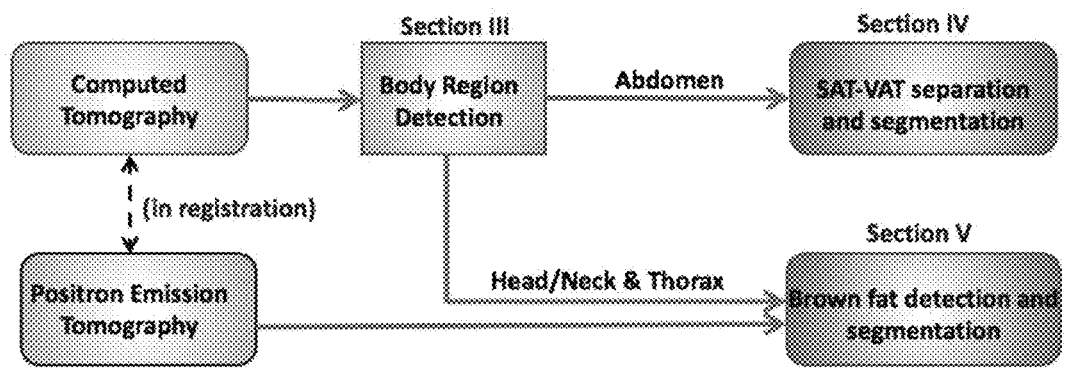
FIG. 2 is a flow diagram of the proposed system for whole-body adiposity analysis. The input to the system comprises PET/CT images. Thorax and abdominal regions are detected using deep learning features in the first stage, followed by Subcutaneous-Visceral adipose tissue segmentation using CT images, and Brown Adipose Tissue detection and quantification using PET images.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

ABBREVIATION LIST

BAT—Brown Adipose Tissue
BMI—Body Mass Index
C3D—Convolutional 3D
CAD—Computerized Automatic Detection
CCA—Canonical Correlation Analysis
CCF—Canonical Correlation Forests
CNN—Convolutional Neural Network
CRF—Conditional Random Fields
CT—Computerized Tomography
dCM—Cramer Von Mises Distance
DSC—Dice Similarity Coefficient
dTV—Total Distance Variation
FDG—Fluorodeoxyglucose
FP—False Positive
HOG—Histogram of Oriented Gradients
HU—Hounsfield Unit
IoU—Intersection over Union
IRB—Institutional Review Board
LoOS—Local Outlier Score
MAD—Median Absolute Deviation
MAE—Mean Absolute Error
MF—Mondrian Forest
MRI—Magnetic Resonance Imaging
PET—Positron Emission Tomography
RANSAC—Random Sample Consensus
RF— Random Forests
ROI—Region of Interest
RW—Random Walk
SAT—Subcutaneous Adipose Tissue
sCCF—Structured Canonical Correlation Forests
SEM—Standard Error of the Mean
SIFT—Scale Invariant Feature Transformation
SUV—Standardized Uptake Value
TAT—Total Adipose Tissue
TP—True Positive
VAT—Visceral Adipose Tissue
WAT—White Adipose Tissue

DEFINITIONS

As used in the specification and claims, the singular form "a", "an" and "the" include plural references unless the context clearly dictates otherwise.

"Subject" is used to describe an animal, preferably a mammal, more preferably a human, on whom the present system and method are used.

The term "about" as used herein is not intended to limit the scope of the invention but instead encompass the specified material, parameter or step as well as those that do not materially affect the basic and novel characteristics of the invention. In some instances, the term "about" refers to ±10%.

"White adipose tissue (WAT)" as used herein refers to a type of fat tissue in mammals which is used mainly for the storage of triglycerides during energy consumption and fatty acid release during energy expenditure. WAT can be used as a source of energy, for heat insulation and as a mechanical cushion.

"Brown adipose tissue (BAT)" as used herein refers to a second type of fat tissue (the first being white adipose tissue) found in mammals which is used mainly to transfer energy from food into heat during the thermogenesis process.

"Visceral adipose tissue (VAT)" as used herein refers to white adipose tissue which is located around inner organs in mammals. VAT in the abdomen can further divided into omental and mesenteric with mesenteric being more deeply buried such as surrounding the intestine.

"Subcutaneous adipose tissue (SAT)" as used herein refers to white adipose tissue which is located beneath the skin in mammals. SAT is less metabolically active than VAT.

"Computerized automatic detection system (CAD)" as used herein refers to a system and method of use thereof for detecting, segmenting, and quantifying WAT and BAT from an imaging scan such as a PET/CT scan or a PET/MRI scan. This system is comprised of two main modules each having a series of steps utilizing various algorithms/equations. The first module consists of steps for separating and quantifying SAT from VAT. The second module consists of steps for detecting and segmenting BAT. An optional third module is available to automatically detecting specific organs containing adipose tissue. Depending on the specific purpose, the modules can operate independently or in combination with each other. In some embodiments, the first and second modules are used together while in other embodiments, all three modules are used together.

"Quantifying" as used herein refers to determining and expressing the quantity of a substance, such as different types of adipose tissues.

"Segmenting" as used herein refers to separating or dividing a substance. In some instances, adipose tissue is divided from other tissues while in other cases, WAT is divided from BAT or VAT is separated from SAT.

"Imaging scan" as used herein refers to a detailed scan or image of the body of a mammal that is obtained using technology such as X-rays, radio waves, magnetic fields, scanners, radiopharmaceuticals, and/or high frequency sound waves. Examples of such scans include, but are not limited to positron emission tomography (PET) scan; computed tomography (CT) scan; magnetic resonance imaging (MRI) scan; positron emission tomography/computed tomography (PET/CT) scan, a positron emission tomography/magnetic resonance imaging scan (PET/MRI) and a contrast-enhanced ultrasound (CEUS) scan.

With obesity being one of the most prevalent health conditions in the world, its quantification especially in the abdominal region is vital. In this regard, the quantification of visceral fat is significant. In parallel, since BAT is found to be negatively correlated with BMI, its quantification is essential for many clinical evaluations including obesity and metabolic syndromes.

The CAD system for image-based quantification of WAT and BAT generally consists of obtaining PET/CT scans of the subject; detecting body region using an algorithm which detects the abdomen and thorax; performing SAT-VAT segmentation and quantification; and performing BAT detection and segmentation. Once the body region of interest is found, Geodesic Flow Kernel (GFK) can be used in a method for organ detection.

For central obesity quantification, the inventors present an unsupervised method for the separation of visceral and subcutaneous fat at the whole-body and body-region levels. In order to keep the proposed method fully automated, the inventors also propose a minimally supervised body region detection method where training was performed on a single subject. The inventors ascribe the improved performance of the method to robust outlier rejection using geometric and appearance attributes followed by context driven label fusion. Evaluations were performed on non-contrast CT volumes from 151 subjects. Experimental results indicate that the proposed system has a great potential to aid in detecting and quantifying central obesity in routine clinical evaluations, obtaining state-of-the-art performance of 94% and 92% dice similarity scores for SAT and VAT delineation, respectively.

For brown fat quantification, the inventors offer a fully automated image analysis pipeline using PET/CT scans. Specifically, the inventors propose a novel approach to automatically detect and quantify BAT from PET/CT scans involving PET guided CT co-segmentation, and a new probabilistic distance metric combining Total Variation and Cramer-von Mises distances. The proposed approach has a potential to assist in the clinical efforts to counteract obesity in the most natural way. The inventors performed extensive evaluations and the methods achieved state-of-the-art performances.

Region Detection in Whole Body CT Volumes

The input to the abdominal region detection algorithm is a whole-body CT volume given by $\mathcal{I} \in \mathbb{R}$ X×Y×Z, where X, Y and Z represent the size of image $\mathcal{I}$ in terms of voxel counts in x, y and z dimensions, respectively. Since it is difficult to get a large amount of annotated data for training in medical imaging applications, one should resort to as few training examples as possible. The proposed region detection method can be considered as an instance of one-shot learning as the learners are trained only on one subject to make predictions for the remaining 150 subjects.

The region detection framework locates two slices in the CT volume, i.e., top and bottom of the region of interest. Detecting these two slices is challenging because they can easily be confused with similarly appearing slices. Therefore, there is a need for a better feature representation. In this regard, deep learning has recently adapted quite successfully for computer vision and medical imaging applications. (Krizhevsky, A., Sutskever, I., Hinton, G. E.: Imagenet classification with Deep Convolutional Neural Networks. In: Advances in Neural Information Processing Systems. pp. 1097-1105 (2012); Shin, H. C., Roth, H. R., Gao, M., Lu, L., Xu, Z., Nogues, I., Yao, J., Mollura, D., Summers, R. M.: Deep convolutional neural networks for computer-aided detection: CNN architectures, dataset characteristics and transfer learning. IEEE Transactions on Medical Imaging 35(5), 1285-1298 (2016)). To benefit from this rich representation of image features, the inventors use Convolutional Neural Network (CNN) features (i.e., deep learning features) as image attributes extracted from the first fully connected layer of Fast-VGG Network. (Chatfield, K., Simonyan, K., Vedaldi, A., Zisserman, A.: Return of the devil in the details: Delving deep into convolutional nets. In: BMVC (2014)). The network comprises 5 convolution layers and 3 fully connected layers. The first, second, and fifth convolution layers are followed by a max-pooling layer by convention. In order to have faster operations, 4-pixels stride is used in the first convolution layer. The dimension of the feature vector generated for each slice is equal to 4096. Given the reference annotations of the body regions for one subject's volumetric image, the inventors find its Euclidean distance with the testing subjects' images using deep learning features. Given the annotation for one subject, the Euclidean distance with the testing subjects is found using deep features. For training, two sets of learners are used: positive (Dp) and negative (Dn). The testing slice $I \in \mathcal{I}$, where I is the testing (image) slice from the whole body CT volume $\mathcal{I}$ corresponding to the smallest distance with the positive set and largest distance with the negative set is selected as the desired result. In order to combine the probabilities pertaining to Dp (positive learner) and Dn (negative learner), logarithmic opinion pooling is used as:

$$P(I) = \frac{1}{Z} P(I \mid D_p)^w P(I \mid D_n)^{1-w} \quad (1)$$

Where P(I) is the probability for testing slice I, P(I|Dp) and P(I|Dn) are the probabilities pertaining to positive and negative learners respectively, $Z = \Sigma P(I \mid D_p)^w P(I \mid D_n)^{1-w}$ is the normalizing constant and w is the weight parameter (i.e., $0 \leq w \leq 1$). (Hinton, G. E.: Products of experts. In: Artificial Neural Networks, 1999. ICANN 99. vol. 1, pp. 1-6. IET (1999)).

SAT-VAT Separation and Quantification

Figure 3:
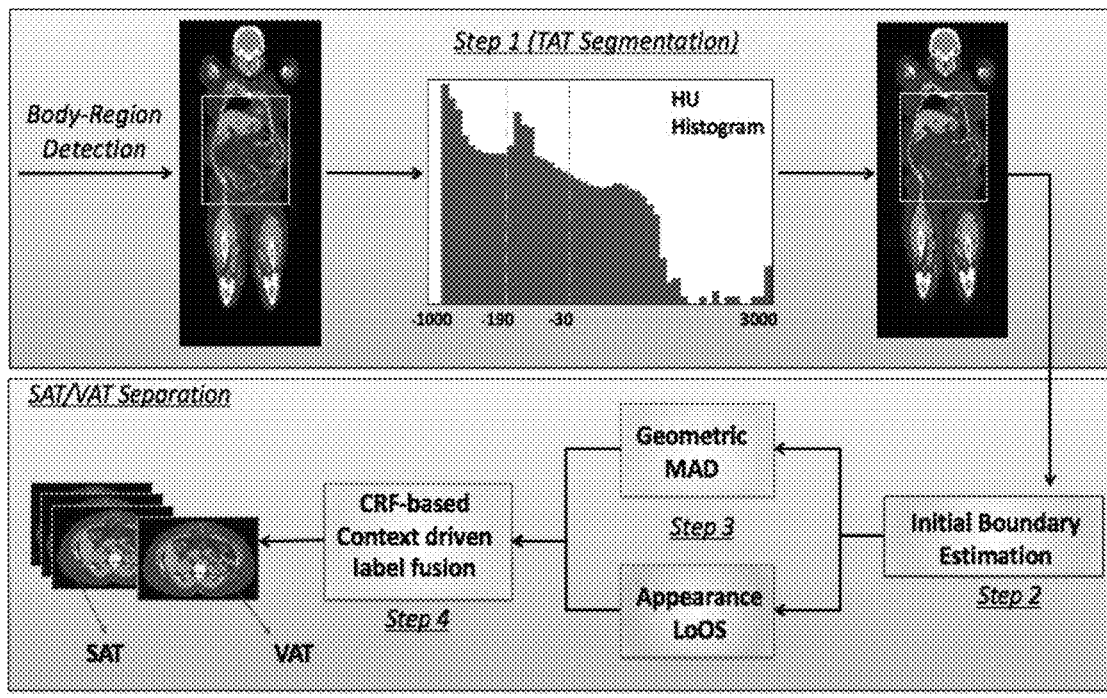
FIG. 3 is an overview of the proposed SAT-VAT separation method. Once the abdominal region is detected. Total Adipose Tissue (TAT) is segmented using CT intensity interval known for fat tissue. Initial Subcutaneous-Visceral adipose tissue boundary is estimated by evaluating multiple hypothesis points. Geometric Median Absolute Deviation (MAD) and appearance based Local Outlier Scores (LoOS) are then combined within the 3D Conditional Random Field (CRF) based label fusion.

Generally, the proposed SAT-VAT separation framework is comprised of the steps illustrated in FIG. 3. Since the HU interval for certain substances such as fat, water, and air in CT remains relatively constant, it is straightforward to identify TAT using a clinically validated thresholding interval on the HU space (Step 1). The initial boundary between VAT and SAT regions is identified in step 2 by conducting a sparse search over a line connecting the abdominal region center with the skin boundary (white dotted line in FIG. 4). In step 3, two refinement methods are presented to remove FP boundary contour points: Median Absolute Deviation (MAD) coefficient and Local Outlier Scores (LoOS). In the final step, the inventors develop a sparse 3D CRF formulation to perform the finest SAT-VAT separation utilizing shape, anatomy, and appearance cues.

SAT-VAT Separation

Step 1: Total Adipose Tissue (TAT) Segmentation

The input to the fat quantification pipeline is the abdominal volume. By following the clinical convention, the automatically detected abdominal CT volume is thresholded by −190 to −30 HU interval to obtain TAT. (Yoshizumi, T., Nakamura, T., Yamane, M., Waliul Islam, A. H. M., Menju, M., Yamasaki, K., Arai, T., Kotani, K., Funahashi, T., Yamashita, S., et al.: Abdominal fat: Standardized technique for measurement at ct 1. Radiology 211(1), 283-286 (1999)) A morphological closing on the input image using a disk with a fixed radius of r is performed followed by a median filtering in an m×m neighborhood to smooth the volume for the next phase.

Step 2: Initial Boundary Estimation

The inventors roughly identify the skin boundary of the abdominal region by selecting the longest isoline in the thresholded image (obtained from Step 1). For each point on the skin boundary contour S={s1, . . . , sn}, the inventors generate a set of hypotheses H={h1, . . . , hu} along the radii connecting S with its centroid C (FIG. 4). Each hypothesis (candidate boundary location) is next verified for the possibility of being a boundary location by assessing image gradient information on the line connecting its location to the centroid C (white arrows in FIG. 4). The SAT-VAT separation boundary, B={b1, . . . , bn}, would satisfy the following condition: hj≠hj−1 for hj∈B, and bi∈H, ∀i. As illustrated in FIG. 4, hypothesis points change their gradients in the close vicinity of B. These boundary points can still be noisy and may get stuck inside the small cavities of the subcutaneous fat. To alleviate such instabilities, a two-stage refinement method is used in Step 4.

Step 3: Outlier Rejection
Geometric MAD:

In the first stage of the outlier removal, the inventors apply median absolute deviation (MAD) on the distances between B and S. The SAT-VAT separation boundary should maintain a smoothly varying distance from the skin boundary. However, the outliers in subcutaneous and visceral cavities usually violate this smooth transition; therefore, the inventors apply median absolute deviation (MAD) on the points between B and S to remove outliers based on the geometric information. (Leys, C., Ley, C., Klein, O., Bernard, P., Licata, L.: Detecting outliers: do not use standard deviation around the mean, use absolute deviation around the median. Journal of Experimental Social Psychology 49(4), 764-766 (2013)) The resulting MAD coefficient $\Phi_i$, for each boundary point, indicates a score for being an outlier:

$$\Phi_i = (|d_i - \text{med}(d)|)(\text{med}(|d_i - \text{med}(d)|))^{-1} \quad (2)$$

where d is the Euclidean distance between S and B, $d_i = \|s_i - b_i\|_2$, and med is the median operator. Boundary locations with high MAD coefficients $\Phi > t$ are labeled as outliers and subsequently removed from B.

Local Outlier Scores:

Although MAD can be quite effective in outlier rejection, there may still be some boundary locations that could potentially lead to drifting of SAT-VAT separation due to limitation of shape/geometry based attributes. To mitigate the influence of those boundary points, the second stage of the outlier rejection is applied which integrates appearance information through Histogram of Oriented Gradients (HOG) features. For each candidate boundary point, its appearance attribute (HOG) computed in a c×c cell is attached. Since candidate boundary points lie on a high dimensional manifold (non-Euclidean), normalized correlation distance is used to compute similarities of those points. This is justified by computing the proximity, $Q_{ij}$ between boundary points $b_i$ and $b_j$ using t-distributed stochastic neighborhood embedding (t-SNE):

$$Q_{ij} = \frac{1 + (\|b_i - b_j\|_2)^{-1}}{\sum_{u \neq v}(1 + (\|b_u - b_v\|_2)^{-1}} \quad (3)$$

(Van der Maaten, L., Hinton, G.: Visualizing data using t-sne. JMLR 9(2579-2605), 85 (2008))

FIG. 5 demonstrates the feature embedding visualization using t-SNE, where better separation of features with normalized correlation distance is observed.

Points that are not mapped together to denser regions in high dimensional feature space are considered as outliers. By following this intuition, local outlier scores (LoOS) H are obtained thus indicating a confidence measure for each point being an outlier:

$$\Pi(x) = \text{erf}\left(\frac{PLOF(x)}{\sqrt{2} \cdot nPLOF}\right) \quad (4)$$

where erf is the Gaussian Error Function, and PLOF is the probabilistic local outlier factor based on the ratio of the density around point x and the mean value of estimated densities around all the remaining points. nPLOF is the λ standard deviation of the PLOF. (Kriegel, H. P., Kroger, P., Schubert, E., Zimek, A.: Loop: local outlier probabilities. In: Proceedings of the 18th ACM conference on Information and knowledge management. pp. 1649-1652. ACM (2009))

Step 4: Context Driven Label Fusion Using 3D CRF

In order to fuse the labels of the boundary candidates across different slices and create a fine SAT-VAT separating surface, the inventors use 3D Conditional Random Fields (CRF). In the CRF formulation, a set of N slices is selected to construct a graph G=(V,E), where the nodes (V) consist of only the hypothesis boundary points (not the image pixels) and the edges (E) join neighboring boundary points in a high dimensional feature space. The labels, i.e., outlier and SAT-VAT boundary, are considered as source and sink in the context of our work.

A CRF formulation comprises of unary and pairwise potentials. The unary potentials of the CRF are defined as the probabilities obtained after applying k-means clustering to the normalized scores of third stage:

$$\Theta e(k_i | v_i) = -\log(P(k_i | v_i)) \quad (5)$$

The pairwise potentials between the neighboring points $v_i$ and $v_j$ are defined as:

$$\Psi(k_i, k_j | v_i, v_j) = \left(\frac{1}{1 + |\phi_i - \phi_j|}\right)[k_i \neq k_j] \quad (6)$$

where $|\cdot|$ is the L1 distance, $[\cdot]$ is the indicator function, and $\phi$ is the concatenated vectorized appearance and geometric features. Once unary and pairwise potentials are defined, the negative logarithm of P(k|G;w) is minimized with k labels (k∈{0, 1}) and weights w as:

$$k^* = \underset{k,w}{\text{argmin}}(-\log(P(k | G; w))) = \\ \underset{k,w}{\text{argmin}}\left(\sum_{v_i \in V} \Theta(k_i | v_i) + w \sum_{v_i, v_j \in E} \Psi(k_i, k_j | v_i; v_j)\right) \quad (7)$$

Equation 7 is solved using graph-cut based energy minimization. (Boykov, Y., Veksler, O., Zabih, R.: Fast Approximate Energy Minimization via Graph Cuts. IEEE Transactions on Pattern Analysis and Machine Intelligence 23(11), 1222-1239 (2001)). Graph-cut for more than two labels is an NP-hard problem and solved using approximate solutions. The inventors have chosen graph-cut for minimizing the energy function defined to solve 3D sparse CRF. In contrast to level sets and loopy belief propagation methods, the graph-cut for two labels returns the global optimum in polynomial time. Additionally, graph cut formulation with a discrete binary solution space of [0,1] after linear programming relaxation (as in equation 7) is a convex problem. After the label fusion stage using 3D CRF, the inventors fit a convex-hull around the visceral boundaries and segment inside the convex-hull is masked as VAT.

SAT-VAT Separation Results

Data: With IRB approval, the inventors retrospectively collected imaging data from 151 subjects who underwent PET/CT scanning (67 men, 84 female, mean age: 57.4). Since CT images are from whole body PET/CT scans (64-slice Gemini TF, Philips Medical Systems); they have low resolution, and no contrast agent was used for scanning. In-plane spacing (xy-plane) of CT image was recorded as 1.17 mm by 1.17 mm, and slice thickness was 5 mm. The scanner parameters for the CT were as follows: 120-140 kV and 33-100 mA (based on BMI), 0.5 s per CT rotation, pitch of 0.9 and 512×512 data matrix was used for image fusion. The field of view (FOV) was from the top of the head to the bottom of the feet. The CT reconstruction process was based on filtered back-projection algorithm. No oral or intravenous contrast was administered.

Subjects were selected to have a roughly equal distribution of varying BMIs in order to have an unbiased evaluation. The evaluation set comprised underweight subjects (N=20), normal subjects (N=50), overweight subjects (N=46), obese subjects (N=35). UB (>10 years of experience in body imaging with CT and PET/CT interpretation) and GZP (>10 years of experience as a nuclear medicine physician and body imaging fellowship in radiology and imaging sciences) segmented fat regions by separating SAT and VAT boundary and using appropriate image post-processing such as edge-aware smoothing. Complementary to this interpretation, the participating radiologist BW (>20 years of experience in general radiology, body imaging, interventional radiology, and oncology imaging) evaluated SAT and VAT separating boundary qualitatively for both interpreters, and their segmentations were accepted at the clinical level of evaluations. This process is currently the most common procedure in creating a reference standard for segmentation evaluation. (Warfield, S. K., Zou, K. H., Wells, W. M.: Simultaneous truth and performance level estimation (STAPLE): an algorithm for the validation of image segmentation. IEEE Transactions on Medical Imaging 23(7), 903-921 (2004); Sabuncu, M. R., Yeo, B. T., Van Leemput, K., Fischl, B., Golland, P.: A generative model for image segmentation based on label fusion. IEEE Transactions on Medical Imaging 29(10), 1714-1729 (2010), Udupa, J. K., Leblanc, V. R., Zhuge, Y., Imielinska, C., Schmidt, H., Currie, L. M., Hirsch, B. E., Woodburn, J.: A framework for evaluating image segmentation algorithms. Computerized Medical Imaging and Graphics 30(2), 75-87 (2006); Kohlberger, T., Singh, V., Alvino, C., Bahlmann, C., Grady, L.: Evaluating segmentation error without ground truth. In: International Conference on Medical Image Computing and Computer-Assisted Intervention. pp. 528-536. Springer (2012)). Above 99% of agreement over Dice Similarity Coefficient (i.e. overlap ratio) was found between observers' evaluations with no statistical difference (t-test, p>0.5).

Parameters and Evaluations Metrics:

The following parameters are noted towards reproducible research for the experiments: r=10, m=λ=3, t=2.5, c=14, w=0.5, and N=5. For evaluation of region detection, the inventors use Intersection Over Union (IoU) given by:

$$\frac{\text{Overlap}(R_G, R_S)}{\max(|R_G|, |R_D|)},$$

where RG and RD are reference standard and automatically detected abdominal regions, respectively. For segmentation evaluation, the inventors use widely accepted Dice Similarity Coefficient (DSC):

$$\frac{2|I_G \cap I_S|}{|I_G| + |I_S|},$$

where $I_G$, $I_S$ are reference standard and automatically segmented fat regions, respectively. Moreover, the inventors use Mean Absolute Error (MAE) to measure volumetric fat difference (in milliliters, mL) between true and segmented fat regions.

Comparisons:

For abdominal region detection, the upper boundary of the region was defined by the superior aspect of the liver, whereas the lower boundary was defined by the bi-furcation of the abdominal aorta into the common iliac arteries. (Udupa, J. K., Odhner, D., Zhao, L., Tong, Y., Matsumoto, M. M., Ciesielski, K. C., Falcao, A. X., Vaideeswaran, P., Ciesielski, V., Saboury, B., et al.: Body-wide hierarchical fuzzy modeling, recognition, and delineation of anatomy in medical images. Medical Image Analysis 18(5), 752-771 (2014)). The proposed region detection method outperforms Scale Invariant Feature Transform (SIFT) flow and CNN with Random Forest methods. (Liu, C., Yuen, J., Torralba, A., Sivic, J., Freeman, W. T.: Sift flow: Dense correspondence across different scenes. In: Computer Vision-ECCV 2008, pp. 28-42. Springer (2008); (Chatfield, K., Simonyan, K., Vedaldi, A., Zisserman, A.: Return of the devil in the details: Delving deep into convolutional nets. In: BMVC (2014)) As can be seen in Table I, the proposed region detection method significantly outperformed registration based methods such as Scale Invariant Feature Transform (SIFT) flow. Moreover, the proposed combination of positive and negative learners (Equation 1) reports 7.9% improvement in IoU and 6.5% reduction in average absolute slice difference as compared only a positive learner with deep learning features.

Moreover, the inventors performed extensive comparisons for SAT-VAT segmentation and quantification. Specifically, the inventors compared their method to One-class SVM, Random Sample Consensus (RANSAC), and a state-of-the-art outlier detection method by Mahito et al., which was based on iterative data sampling. (Zhao, B., Colville, J., Kalaigian, J., Curran, S., Jiang, L., Kijewski, P., Schwartz, L. H.: Automated quantification of body fat distribution on volumetric computed tomography. Journal of computer assisted tomography 30(5), 777-783 (2006); Fischler, M. A., Bolles, R. C.: Random sample consensus: a paradigm for model fitting with applications to image analysis and automated cartography. Communications of the ACM 24(6), 381-395 (1981); Sugiyama, M., Borgwardt, K.: Rapid distance-based outlier detection via sampling. In: Advances in Neural Information Processing Systems. pp. 467-475 (2013)) In addition, the inventors have progressively shown the results of the proposed framework's individual steps to provide progressive improvement in accuracy, i.e., Geometric MAD, Appearance LoOS, and the final context driven fusion using sparse 3D CRF. Two delineations from expert interpreters were considered for the segmentation evaluation of SAT and VAT.

Figure 7:
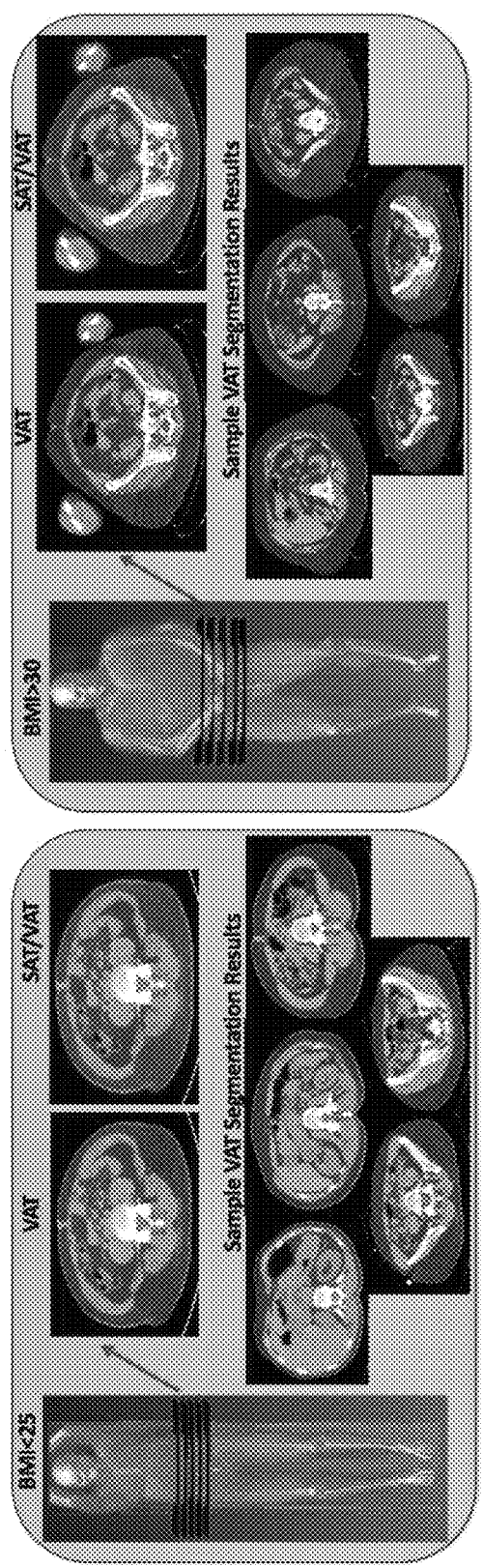
FIG. 7 is an image depicting Visceral Adipose Tissue (red) and Subcutaneous Adipose Tissue (green) segmentations are illustrated for two subjects (one with BMI<25, another with BMI>30) at the chosen abdominal slice level along with their volume renderings. Several abdominal slices are also shown for central adiposity accumulation.

FIG. 7 shows the volume rendering of subjects along with VAT and SAT delineations for qualitative evaluation. Highly accumulated VAT in obese subjects is observed. DSC and MAE results for SAT and VAT are shown in Table II where significant improvement compared to other methods is obtained. The proposed method records around 40% lesser MAE as compared to other methods.

TABLE I

Abdominal region detection results measured by Intersection over Union (higher the better) and average absolute slice difference (lower the better) along with standard error of the mean (SEM):

| Methods | IoU (SEM) | Avg. Abs. slice diff. (SEM) |
|---|---|---|
| SIFT Flow [39] | 0.263 (0.019) | 90.22 (2.71) |
| Deep learning features [26] with Positive learner only | 0.744 (0.016) | 50.28 (0.66) |
| Proposed method (Equation 1) | 0.803 (0.014) | 47.01 (0.62) |

TABLE II

Segmentation and quantification results for SAT and VAT evaluated by Dice Similarity Coefficient (higher the better) and Mean Absolute Error (lower the better) along with standard error of the mean (SEM):

| Methods | SAT DSC (SEM) | VAT DSC (SEM) | SAT MAE in mL (SEM) | VAT MAE in mL (SEM) |
|---|---|---|---|---|
| One-class SVM | 0.886 (0.004) | 0.842 (0.006) | 16.695 (0.963) | 16.696 (0.963) |
| Zhao et al. [13] | 0.895 (0.003) | 0.840 (0.004) | 11.183 (0.350) | 11.184 (0.350) |
| RANSAC [41] | 0.913 (0.003) | 0.861 (0.005) | 14.126 (1.179) | 14.126 (1.179) |
| Mahito et al. [42] | 0.871 (0.003) | 0.825 (0.006) | 18.331 (1.230) | 18.331 (1.229) |
| Geometric MAD | 0.896 (0.006) | 0.876 (0.005) | 13.665 (0.872) | 13.666 (0.872) |
| Appearance LoOs | 0.925 (0.002) | 0.885 (0.004) | 11.815 (0.857) | 11.816 (0.856) |
| Proposed method | 0.943 (0.003) | 0.919 (0.003) | 6.703 (0.466) | 6.706 (0.466) |

Computation Time:

The computation time for SAT-VAT segmentation method was less than 2 s/slice using the claimed method, and less than 2.5 s/slice in other methods that were compared. The unoptimized MATLAB implementation of Geometric MAD took approximately 0.45 s/slice, that of appearance LoOS ran on average in 0.71 s/slice, followed by an average of 1.96 s/slice for 3D CRF on Intel Xeon Quad Core CPU @ 2.80 GHz and 24.0 GB RAM. Note also that none of the methods (in the comparison experiments) required any manual intervention.

Brown Fat Detection and Segmentation

Figure 6:
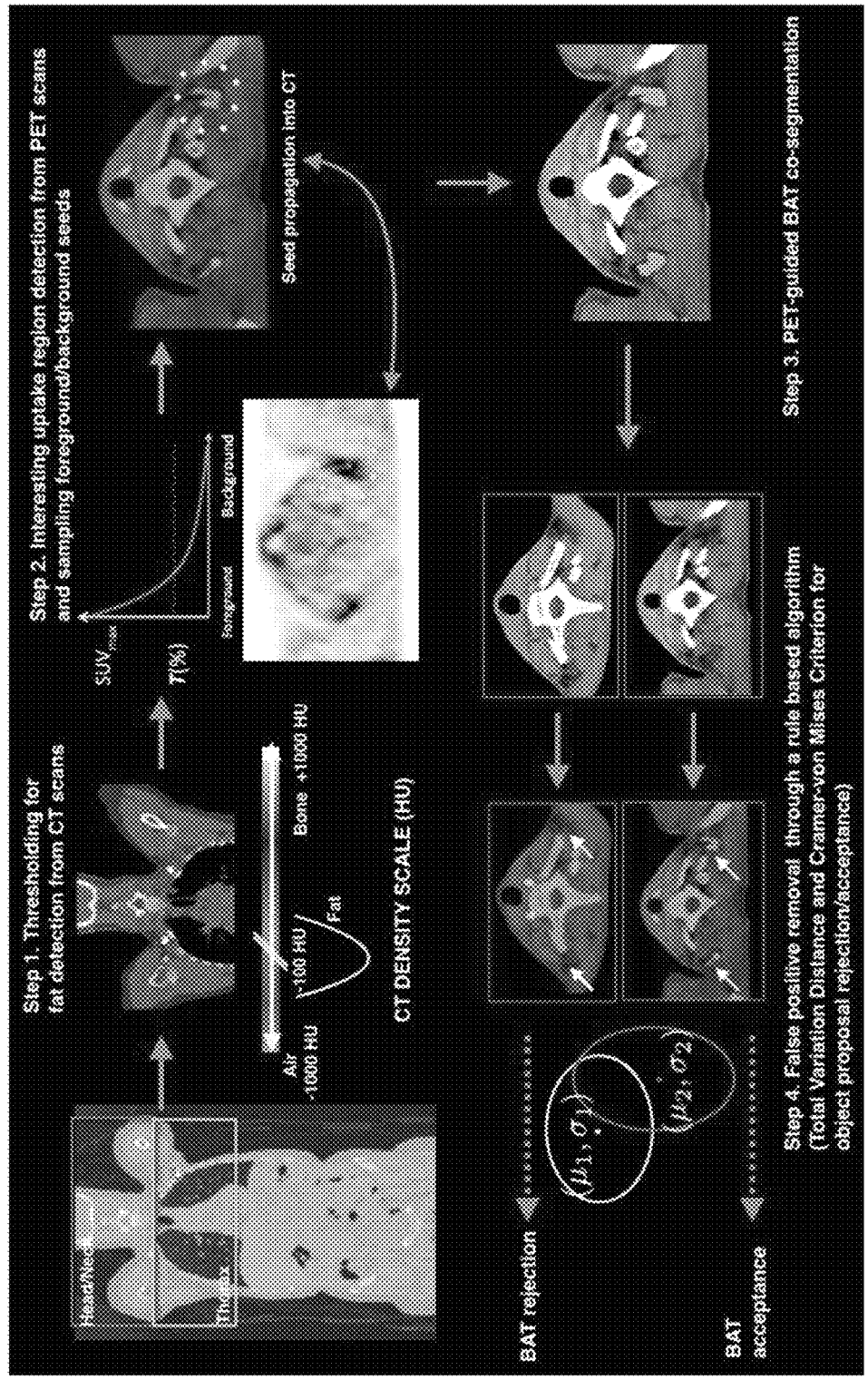
FIG. 6 is an image depicting an overview of the proposed Brown Adipose Tissue (BAT) detection and segmentation system. Given the head-neck and thorax regions, adipose tissue is identified using CT thresholding intervals (Step 1). Using the corresponding PET scans, segmentation seeds are sampled in accordance with high uptake regions (Step 2). PET-CT co-segmentation is performed using Random Walk (Step 3) followed by false positive removal (Step 4) using Total Variation and Cramer-von Mises distances.

The proposed BAT detection and delineation algorithm initiates with the segmentation of fat tissue from CT, followed by an automatic seed selection for BAT. The inventors then performed PET guided CT co-segmentation and lastly propose a false positive rejection method. These 4 steps are depicted in FIG. 6.

Briefly, to detect, segment and quantify brown fat automatically from PET/CT scans, canonical random forests with structure cues are used for automatic body region detection. This allows the algorithm to be constrained to potential BAT regions only (head/neck and thorax). Next, a fixed HU interval filtering is used to identify all adipose tissue (white and brown) from CT images. Next, a seed sampling scheme is used for extracting foreground and background cues from high uptake regions of PET images. Identified seeds are then propagated into the CT images using one-to-one correspondence with PET images. Next, a PET-guided image co-segmentation algorithm is initiated on the hyper-graph (PET/CT) to delineate potential BAT regions. Finally, a new probabilistic metric combining total variation and Cramer-Von Mises distances is implemented in order to differentiate BAT regions from non-BAT regions as a false positive rejection step.

The proposed system achieves highly accurate region detection rates of 97.5% and 90.53% for head/neck and thorax regions, respectively. The sensitivity and specificity for BAT segmentation are found to be 92.3±10.1% and 82.2±18.9%/, respectively. The differentiation between BAT and non-BAT regions is achieved with an accuracy of 99.1%.

Automatic Body Region Detection from CT Scans

Due to their competitive predictive performance, random forests (RF) are widely used for classification as well as regression tasks in medical imaging analysis. However, RF-based classifiers require a large batch of training samples to generate accurate and robust results. To avoid this necessity and have a fast automatic body region detection, the inventors used Canonical Correlation Forests (CCF) that are not restricted to the coordinate system of the input features and are trained using Canonical Correlation Analysis (CCA). (Rainforth, T., Wood, F.: Canonical correlation forests. arXiv preprint arXiv: 1507.05444 (2015)) Unlike in RF, trees in CCF are not restricted to be axis-aligned and hence they are flexible to incorporate the correlation between features. CCA is carried out between the features and classes prior to split selection. The split is selected by an exhaustive search in the projected feature space. Structural cues are also incorporated into the training of CCF to define a better scoring function. (Lakshminarayanan, B., Roy, D. M., Teh, Y. W.: Mondrian forests: Efficient online random forests. In: Advances in Neural Information Processing Systems. pp. 3140-3148 (2014))

Forest Definition, Notation, and Feature Extraction

The goal in body region detection is to predict class labels $y_n \in \{1, \ldots, L\}$ given a vector of input imaging features $x_n \in R$ D for each data point $n \in \{1, \ldots, N\}$. In the implementation, 2-class classification is focused on such that body-region boundaries are trained against all the other definitions (1-versus-all). Let $Y=\{y_n\}$ N n=1 denote the set of labels and $X=\{x_n\}$ N n=1 be the set of feature vectors and suppose $T=\{t_i\}, i=1 \ldots F$ represents forest with F binary trees each represented by $t_i$. Each $x_i$ is a 512 dimensional GIST feature vector, shown to be quite robust for general image classification tasks. (Oliva, A., Torralba, A.: Modeling the shape of the scene: A holistic representation of the spatial envelope. International journal of computer vision 42(3), 145-175 (2001)) The class vector $Y \in R$ N×1 is transformed into an sparse matrix $Y \in I$ N×L such that $Y_{n1}=1$, when n belongs to class 1. For finding the split point during training, CCA is applied to X and Y represented as: Φ=CCA(X, Y), where Φ are the canonical coefficients. After getting the classification scores ω for testing slices from CCF, the inventors use structural information from the training data to refine the prediction. The top c predictions are picked for each of the top and bottom of the thorax region (note that top slice of thorax is the bottom of head/neck region). This leads to c×c possible configurations. The scoring function s for a configuration C is given by equation 1, where Ri and Rj are top and bottom of the region of interest, respectively, uij is the mean displacement from top to bottom of the region of interest from the training data and λ is the weight parameter.

Segmentation and Quantification of BAT

Step 1: Segmenting Fat Tissue from CT Scans

Standard reference for estimating fat tissues in CT is by means of the computed planimetric method or with a fixed attenuation range from −190 to −30 HU. In the implementation, the inventors have extended this range into [−250, −10] HU to be more inclusive. Prior to this operation, the inventors employed a 3D median filtering to smooth the images. Resulting segmentations form a basis for differentiating BAT from non-BAT regions.

Step 2: Automatic Seed Selection

BAT regions are metabolically active, and studies reported that at least an S U $V_{max}$=2 g/ml was observed in BAT regions. (Muzik, 2013 and Cohade 2003). However, it is important to note that $^{18}$F— FDG doesn't only attach to BAT but to tumor regions as well; hence, high SU $V_{max}$ does not necessarily indicate BAT presence. To accurately characterize BAT, the anatomical/structural counterpart of the PET images is required. Since the BAT regions have SU $V_{max}$≥2 g/ml, the head/neck and thorax regions were thresholded accordingly by following the automated seeding module of the joint segmentation method. (Bagci, U., Udupa, J. K., Mendhiratta, N., Foster, B., Xu, Z., Yao, J., Chen, X., Mollura, D. J.: Joint segmentation of anatomical and functional images: Applications in quantification of lesions from PET, PET-CT, MRI-PET, and MRI-PET-CT images. Medical Image Analysis 17(8), 929-945 (2013)). The resulting thresholded PET images most likely include numerous disconnected regions since many pixels may have SUV larger than 2 g/ml due to high metabolic activities. For each disconnected region, pixels with maximum SUVs are defined as foreground seeds. In order to set background pixels, the inventors explored the neighborhood of foreground pixels by searching in 8-directions. Background locations were found by marking the first pixel with less than or equal to 40/o of the SUV$_{max}$ (i.e., conventional percentage for clinical PET thresholding). Those pixels are set as background seeds. The final step is to insert additional background seeds into the pixels lying in the spline connecting background seeds as explained in Bagci, 2013. Once the background and foreground seeds are identified, Random Walk (RW) co-segmentation is employed by solving equation 9 for the unknown labels of the pixels (nodes).

Step 3: PET-Guided Random Walk Image Co-Segmentation

It is reasonable to consider BAT boundary determination process as a co-segmentation problem where the contributions of PET and CT in segmentation procedure are unequal. Inspired by the co-segmentation study by Bagci et al. 2013, the inventors introduce a PET-guided RW co-segmentation algorithm with asymmetric weights. This is based on the fact that the influence of PET on BAT segmentation results is higher than that of CT.

PET and CT images are in registration owing to PET/CT scanner's hybrid reconstruction properties. Any inconsistencies due to breathing and different timing of PET and CT imaging in the PET/CT scanner are minimized using deformable image registration as a post-processing step. Since PET and CT have one-to-one correspondence, thanks to the nature of PET/CT scanning, two graphs pertaining to CT and PET, $G^{CT}=(V^{CT}, E^{CT})$ and $G^{PET}=(V^{PET}, E^{PET})$, can be combined to define a hypergraph $G^H=(V^H, E^H)$, on which the co-segmentation algorithm is applied. Note that for each image, the inventors define a connected undirected graph G with nodes v∈V and edges e∈E⊆V×V Since performing a random walk on the product graph $G^H$ is equivalent to performing a simultaneous random walk on the graphs $G^{CT}$ and $G^{PET}$, the inventors define the nodes and edges as follows:

$$V^H=\{(v_i^{CT},v_i^{PET}):v_i^{CT}\in V^{CT} \wedge v_i^{PET}\in V^{PET}\},$$

$$E^H=\{((v_i^{CT},v_i^{PET}),(v_j^{CT},v_j^{PET})):(v_i^{CT},v_j^{CT})\in E^{CT} \wedge (v_i^{PET},v_j^{PET})\in E^{PET}\}. \quad (8)$$

Similarly, the combinatorial Laplacian matrix definition $L^H$ (that includes labeled and unlabeled nodes as well as weight parameters w of the imaging data) of the product graph $G^H$ is updated from conventional RW formulation to co-segmentation as $L^H=(L^{CT})^\alpha \otimes (L^{PET})^\theta$, where α and θ are constants, 0≤α, θ≤1, and ⊗ denotes direct product. Lastly, probability distribution of intensity values for the product lattice $x^H$ is defined as the direct multiplication of initial probability distribution of $x^{CT}$ and $x^{PET}$ as $x^H=(x^{CT})^\zeta \otimes (x^{PET})^\eta$, where ζ and η are used to optimize the initial probability distributions subject to the constraint 0≤ζ, η≤1. The desired random walker probabilities are then the solution of the combinatorial Drichlet problem as:

$$D[x^H] = \frac{1}{2}(x^H)^T L^H x^H = \frac{1}{2}\sum_{e_{ij}\in E^H} w_{ij}^H (x_i^H - x_j^H)^2 \quad (9)$$

where a combinatorial harmonic function of $x^H$, satisfying the Laplace equation $\triangledown^T x^H=0$, minimizes Eq. 9. To emphasize the effect of PET more than that of CT for BAT region delineation, the inventors select combination of (α, θ) as (0.05, 0.95) and (ζ, η) as (0.3, 0.7) after various empirical evaluations.

Step 4: Differentiating BATs from Non-BAT Regions

BAT regions are not easily separable from other fat regions in CT because WAT and BAT follow the same intensity distributions (fixed HU interval). Conventionally, intensity values of fat regions can be considered to follow a normal distribution with known mean μ and variation σ, (i.e., C=N(μ, σ)). Assume that an uptake region segmented from PET images is $r^{PET}$. Since there is a one-to-one correspondence between CT and PET images then, $r^{PET}=r^{CT}$. The inventors next formulate the problem of differentiating BAT from non-BAT regions as follows. The intensity distribution p, obtained from $r^{CT}$ correspondence of each segmented uptake region $r^{PET}$, should be in the close vicinity of C, i.e., d(p, C)<ε, where d∈[0, 1] is a distance metric measuring whether p belongs to some class of distribution C or not. The inventors postulate that p is sufficiently far from C when lymph nodes, tumor regions, or other non-fat tissues involve in $r^{CT}$.

For the probabilistic distance metric in the framework (d), the inventors propose to use two complementary distance measures: total distance variation ($d_{TV}$) and Cramer Von Mises distance $d_{CM}$. $d_{TV}$ is equivalent to the L1-norm and can be formulated as half of the L1-distance:

$$d_{TV} = \tfrac{1}{2} \Sigma_{x \in \Omega} |p(x) - C(x)| \tag{10}$$

where $\Omega$ is a measurable space on which p and C are defined. Complementary to $d_{TV}$, the inventors also use $d_{CM}$ to judge the goodness of fit between two distributions by emphasizing $L_2$-distance. In other words, $d_{CM}$ is effective in situations where two distributions under comparison have dissimilar shapes (although similar mean and variation can still be captured with $d_{TV}$). The Cramer-von Mises statistics is defined as $$d_{CM} = \min_x |P(x) - \psi(x)| \tag{11}$$

where $\psi(x)$ and $P(x)$ are cumulative distribution functions of $C(x)$ and $p(x)$, respectively. The proposed distance d is simply formed by integrating $d_{CM}$ and $d_{TV}$ as:

$$d = \sqrt{d_{CM}^2 + d_{TV}^2} \tag{12}$$

If $d < \epsilon$, the differentiation system accepts the BAT proposal/hypothesis. Note also that d is a distance-metric because (i) it is symmetric ($d(C, p) = d(p, C)$), (ii) non-negative (as it spans from 0 to 1, $d \geq 0$), (iii) $d(p, C) = 0$ only when $p = C$, and (iv) it satisfies triangle equality as:

$$d(p,C) \leq d(p,D) + d(D,C) \tag{13}$$

Brown Fat Detection and Delineation Results

Data for Quantification of BAT.

This retrospective study was institutional review board (IRB) approved and the need for written informed consent was waived. Thirty-seven adult (>21 years) oncology patients with FDG BAT uptake were identified from PET/CT studies from 2011-2013. The control cohort consisted of 74 adult oncology patients without detectable FDG BAT uptake matched for BMI/gender/season. The oncology patients have malignant tumors which were all biopsy proven. From the 4,458 FDG PET/CT reports in our database, there were 46 unique adult patients whose PET/CT reports specified the presence of BAT. Eight patients were excluded for only negligible PET/CT evidence of BAT reported in the paravertebral region. Another patient was excluded since FDG uptake was associated with interatrial lipomatous hypertrophy. Apart from these, the final selection of PET/CT scans was confirmed based on the consensus agreement of the participating nuclear medicine physicians, radiologist, and clinician. A total of 37 cases of adult BAT patients without FDG avid liver lesions were included in this study.

An intravenous injection of 5.18 MBq/kg (0.14 mCi/kg) $^{18}$F-FDG was administered to patients with a blood glucose level ≤200 mg/dL after fasting for at least four hours. Patients sat in a quiet room during the 60 minute uptake phase and were instructed to remain quiet and refrain from physical activity. All scans were acquired using a Gemini TF (Philips Medical Systems) PET/CT scanner. There were no statistically significant differences between the two cohorts in gender, race, BMI, height, and weight (p>0.05). The voxel dimensions in PET scans were 4 mm×4 mm×4 mm. The PET component of the PET/CT scanner was composed of lutetium-yttrium oxyorthosilicate (LYSO)-based crystal. Emission scans were acquired at 1-2 min per bed position. The FOV was from the top of the head to the bottom of the feet. The three-dimensional (3D) whole-body acquisition parameters were 144×144 matrix and 18 cm FOV with a 50% overlap. The reconstruction process in the scanner was based on the 3D Row Action Maximum Likelihood Algorithm (RAMLA).

To develop the reference standard, the inventors used the manual delineation from three experts. First, the participating nuclear medicine physicians (MO: >20 years of experience, GZP:>10 years of experience, and AG: >10 years of experience), agreed on the predetermined SUV cut-off. GZP segmented the BAT regions, blind to consensus segmentation of MO and AG. Therefore, two delineations were considered in the evaluation, although three experts worked for the segmentation of BAT regions. When segmenting the BAT area, interpreters were pro-vided viewer/fusion software, as well as manual, automated, and semi-automated contouring methods. The interpreters used both CT images (to define anatomical sites and fat tissue with the predefined HU interval) and PET images (with 2.0 g/ml of cut-off S U V$_{max}$) when delineating BAT regions. The fusion of PET with thresholded CT images provided uptake only in fat regions, removing most of the false positive uptake regions from consideration. Next, the interpreters used thresholding on PET uptake within an ROI (roughly drawn by the experts using manual contouring tool) for each detected BAT region. Finally, expert interpreters performed necessary corrections on the segmented PET uptake using manual contouring tools guaranteeing that the segmentations do not overlap with muscle, lymph nodes, and tumors.

Evaluation of Thorax Region Detection.

Anatomically, head-neck/thorax region was defined from the superior aspect of the globes to 5 mm below the base of the lungs. (Udupa, J. K., Odhner, D., Zhao, L., Tong, Y., Matsumoto, M. M., Ciesielski, K. C., Falcao, A. X., Vaideeswaran, P., Ciesielski, V., Saboury, B., et al.: Body-wide hierarchical fuzzy modeling, recognition, and delineation of anatomy in medical images. Medical Image Analysis 18(5), 752-771 (2014)). The inventors used Intersection Over Union (IoU) as the region detection evaluation metric. Table III shows comparative evaluations of different methods with the proposed positive and negative learners. The percentage improvement of 22.4% in IoU was observed over SIFT Flow whereas the IoU increases around 10% in comparison with RF over deep features. (Liu et al. 2008) Moreover, combination of positive and negative learners using logarithmic opinion pooling led to the percentage improvement of further 3% over the instance when only a positive learner was used.

TABLE III

Head-neck and Thorax Region detection results measured by Intersection over Union IoU) and average absolute slice difference along with standard error of the mean (SEM)

| Methods | IoU (SEM) | Avg. Abs. slice diff (SEM) |
|---|---|---|
| SIFT Flow [39] | 0.589 (0.022) | 65.47 (4.29) |
| Deep learning features [26] with Positive learner only | 0.721 (0.018) | 37.59 (3.05) |
| Proposed method (Equation 1) | 0.743 (0.006) | 34.52 (1.28) |

Table IV shows comparative evaluations of different RF classifiers and their performances over different number of trees when detecting thorax regions. While there were no significant differences observed between detection accuracies of RF and MF classifiers, the CCF and sCCF outperformed the other two classifiers. It is worth noting that MF can be more efficient than others if the problem is defined in an online manner. Note also that top slices of the head/neck regions were detected with an accuracy of 100% since it is the first anatomical slice in CT volume. Average detection performance for the head/neck region was then calculated as averaging this performance with the region detection accuracy of the top slice of thorax region (bottom slice of the head/neck). Resulting accuracy was found to be 97.5%.

two regions: head/neck and thorax. After determining the body region, the inventors can use automatic organ detection for each region, and find tightest enclosing box including the organ of interest. Once organs are found, the amount of fat in the detected organs (due to HU interval) can be assigned to that organ's fat volume label.

TABLE IV

Automatic body region detection results measured by Intersection over Union (IoU) with respect to different classifiers and number of trees

| | Classifier # of Trees | | | | | | | | | | | |
|---|---|---|---|---|---|---|---|---|---|---|---|---|
| | RF(%) | | | MF(%) | | | CCF(%) | | | sCCF(%) | | |
| | 50 | 100 | 200 | 50 | 100 | 200 | 50 | 100 | 200 | 50 | 100 | 200 |
| IoU | 86.73 | 88.87 | 88.69 | 85.71 | 85.46 | 88.94 | 88.29 | 89.60 | 89.60 | 89.76 | 90.69 | 91.14 |
| Average IoU | | 88.09 | | | 86.70 | | | 89.26 | | | 90.53 | |

The most accurate results were obtained when CCF and sCCF were used. RF: Random Forest, MF: Mondrian Forest, CCF: Canonical Correlation Forest, sCCF: structured CCF.

Evaluation of BAT Segmentation.

Figure 8:
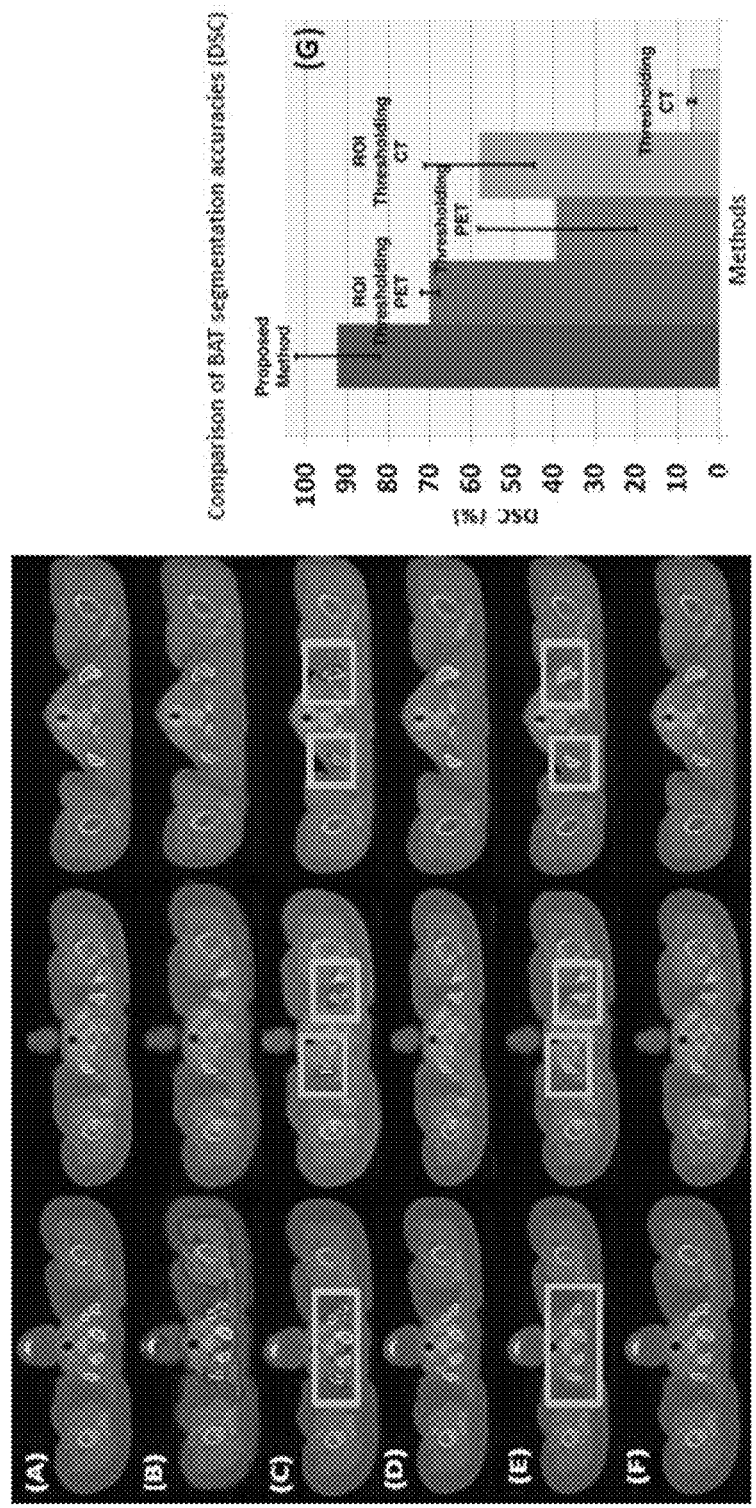
FIG. 8A-G is a series of images depicting for three different anatomical levels (columns), row (A) shows reference standards (white); row (B) demonstrates the results from CT thresholding where pink (inner) and blue (outer) contours show brown fat delineation (blue contour shows fat region near skin boundary which leaks into the body cavity and also overlaps with pink contour as in the first column); row (C) comprises the results from ROI (Region of Interest) based CT thresholding, where orange boxes show user drawn ROIs and blue contours are the brown fat delineation results; row (D) shows the results from conventional PET thresholding, where green contours show output BAT delineations; row (E) depicts the ROI based PET thresholding; and row (F) demonstrates the proposed algorithm's delineation results using PET and CT jointly. (G) Dice Similarity Coefficients (DSC) of the proposed method in comparison with ROI based PET thresholding, PET thresholding, ROI based CT thresholding, and CT thresholding methods are shown.

For quantitative evaluation of the delineation component of the proposed system, the inventors compared True Positive (TP) and False Positive (FP) volume fractions of the segmented tissues with the manual delineation of the experts, blinded to their evaluations. For an unbiased comparison, the inventors computed the average performance over two delineations (Sensitivity (TP): 92.3+/−10.1%, Specificity (100-FP): 82.2+/−18.9%). Metabolic volumes derived by the proposed segmentation were correlated with expert derived volumes, and the resulting correlation coefficient, after linear regression, was found to be $R2=0.97$, $p<0.01$. Example segmentation results at three different anatomical locations are shown in FIG. 8A-F for qualitative evaluations. In the ROI based methods, ROIs were drawn by the user (expert annotator) to "roughly" include BAT regions, while excluding the rest (FIGS. 8C and E).

Comparison to Other Approaches.

The inventors compared the method with the conventional thresholding approaches both at CT and PET (for SUV>2 g/ml) and then applied the logical AND operation to the two masks, followed by a manual false positive (FP) removal step as these are the methods used in available studies to measure BAT boundary and volume. (Muzik et al. 2013) FIG. 8G compares DSC of the proposed method with respect to the baseline methods. The proposed system outperforms other methods by a significant margin.

Evaluation of BAT Region Proposal.

For detection accuracy of the proposed system, the inventors computed True Positive (TP) and False Positive (FP) ratios over 111 PET/CT scans, each labeled as either BAT-positive or BAT-negative. The results showed that in 110 out of 111 scans (99.1%), BAT proposals' acceptance/rejection worked quite well. In only one scan, the system identified one region as non-BAT while the region was originally BAT. This false identification was due to significantly smaller size of the BAT region (<4 mm), potentially owing to the partial volume effect.

Automatic Organ Detection Using Deep Learning and Transferability of Deep Features.

As discussed above, VAT/SAT separation is employed in the abdominal region while BAT presents itself mainly in In performing organ detection, deep learning strategies are used. However, given the large number of volumes to be trained for testing the deep learning algorithms, it is not feasible to train and test each deep learning algorithm independently. Instead, the inventors learn the deep features needed in the training of pre-trained networks available in the literature and transfer those features into medical scans for organ detection as described below.

The objective in a 3D organ detection task is to localize the organ in a bounding volume given the complete 3D CT scan of the subject. As full body scanning using CT remains the most viable option (as well as clinical standard) for screening, tumor detection, characterization and diagnosis, the importance of computer aided diagnosis algorithms to quickly localize the region of interests is vital. Therefore, organ detection is instrumental in different diagnosis and prognosis tasks. It is considered to be the first step in performing robust organ segmentation since an improvement in organ detection methods leads to a significant leap in organ segmentation performance.

The related work in organ detection can be divided into classification and regression-based methods. Criminisi et al. propose a regression forest based approach where each voxel votes for the relative offsets of all bounding boxes. (Antonio Criminisi, Duncan Robertson, Ender Konukoglu, Jamie Shotton, Sayan Pathak, Steve White, and Khan Siddiqui. Regression forests for efficient anatomy detection and localization in computed tomography scans. Medical image analysis, 17(8):1293-1303, 2013) This approach suffers from strong local bias and would lead to drifting of detection results in cases of large inter subject variations.

Work by Lu et al. uses marginal space learning to estimate the position and orientation of the organ followed by refinement measured by JS divergence. The method relies on the scenario where extensive annotated training data from the same domain is available. However, it is impractical that the extensive amount of training data needed from the same domain will always be available thus limiting the applicability of this method. (Chao Lu, Yefeng Zheng, Neil Birkbeck, Jingdan Zhang, Timo Kohlberger, Christian Tietjen, Thomas Boettger, James S Duncan, and S Kevin Zhou. Precise segmentation of multiple organs in ct volumes using learning-based approach and information theory. In Medical Image Computing and Computer-Assisted Intervention-MICCAI 2012, pages 462-469. Springer, 2012.)

Following the popularity of deep learning in generic object detection and classification tasks, Yan et al. opted for a multi-instance CNN for body part recognition in 2D. (Zhennan Yan, Yiqiang Zhan, Zhigang Peng, Shu Liao, Yoshihisa Shinagawa, Dimitris N Metaxas, and Xiang Sean Zhou. Bodypart recognition using multi-stage deep learning. In Information Processing in Medical Imaging, pages 449-461. Springer, 2015.)

Figure 9:
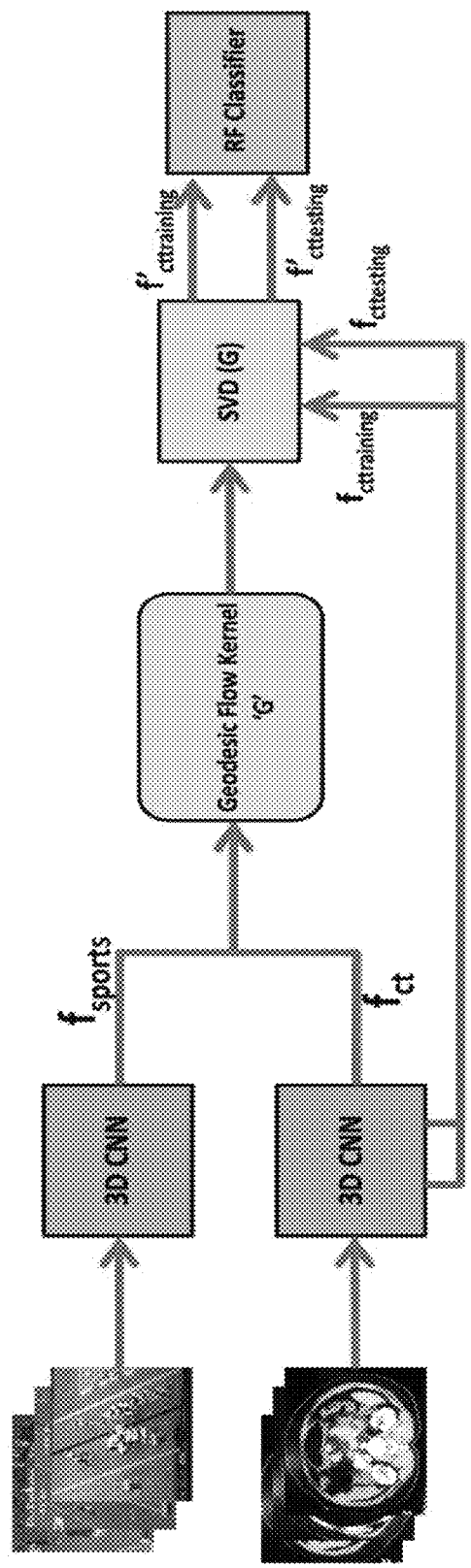
FIG. 9 is an image depicting the work flow of the proposed organ detection method. CNN features are extracted from a random sample of 1 million sports video dataset and from CT volumes. Geodesic flow kernel captures the mutual information between the two feature sets; which is then applied on the training and testing CT data to find the final detection using Random Forest.

In contrast to the methods described above, the inventors explore the transferability of 3D CNN features trained for action recognition tasks to be used for organ detection in 3D CT scans. As the medical imaging data is less readily available than that for action recognition, it is important to measure the adaptability of data across heterogeneous domains which have different distributions and labels. FIG. 9 shows the work flow of the proposed approach.

Geodesic Flow Kernel:

The inventors use Geodesic Flow Kernel to find the transformation from source data to the target data. (Boqing Gong, Yuan Shi, Fei Sha, and Kristen Grauman. Geodesic flow kernel for unsupervised domain adaptation. In Computer Vision and Pattern Recognition (CVPR), 2012 IEEE Conference on, pages 2066-2073. IEEE, 2012.) The geodesic flow $\phi(t)$ between the source HS and the target subspaces HT can be written as $\phi(t)=H_S U_1 \Gamma(t) - R_S U_2 \Sigma(t)$, where U1,U2 are orthonormal matrices, $\Gamma$, $\Sigma$ are the diagonal matrices and $R\_S^T H\_S=0$.

The geodesic flow kernel is defined as the inner product between the projections of input feature vectors onto $\phi(t)$. The source data comprises of randomly sampled 5000 videos from Sports 1 million dataset which has 487 classes. (Andrej Karpathy, George Toderici, Sachin Shetty, Tommy Leung, Rahul Sukthankar, and Li FeiFei. Large-scale video classification with convolutional neural networks. In Computer Vision and Pattern Recognition (CVPR), 2014 IEEE Conference on, pages 1725-1732. IEEE, 2014.) The inventors pass these videos through C3D (Convolutional 3D) to obtain 4096 dimensional feature vector for each video. (Du Tran, Lubomir Bourdev, Rob Fergus, Lorenzo Torresani, and Manohar Paluri. C3d: generic features for video analysis. arXiv preprint arXiv:1412.0767, 2014.) The inventors follow a similar procedure for CT dataset to obtain one feature vector for each possible bounding volume. For the target data, the inventors only use those volumes which are labeled as organ in order to capture the variance in the data.

Experiments:

The inventors performed evaluation on 35 low resolution full body CT volumes having in-plane resolution (x-y plane) of 1.17 mm by 1.17 mm and slice thickness of 5 mm. Training data comprised of 25 volumes where 10 volumes were reserved for testing having liver, left kidney, right kidney and background as classes. The training data for Random Forest comprised of around 50,000 samples, whereas each testing volume has about 10,000 samples for testing. (Leo Breiman. Random forests. Machine learning, 45(1):5-32, 2001)

The inventors use average precision and organ detection rate (ODR) as the evaluation metrics. For ODR, an organ is categorized as detected if at least one of the detection hypotheses has more than 0.4 overlap with the manual annotation. Table V shows quantitative results on these metrics. As can be seen, an average of 10% improvement is obtained with the use of GFK indicating the potential of transferability of 3D CNN features from non-medical domain into challenging medical domain. In this regard, to the best of knowledge, the inventors address for the first time an important problem in computer aided diagnosis system on medical data through deep learning strategies.

TABLE V

Organ Detection Results With and Without Transfer Learning

| Methods | Average Precision | Organ Detection Rate |
|---------|-------------------|----------------------|
| Original | 23.43% | 33.33% |
| Proposed | 30.53% | 43.33% |

CONCLUSIONS

SAT-VAT Separation

The inventors have presented a novel approach to automatically detect abdominal region and separate SAT and VAT for central obesity quantification having improved performance over the current technologies used due to robust outlier rejection using geometric and appearance attributes followed by the context driven label fusion. Evaluations were performed on non-contrast CT volumes from 151 subjects and experimental results indicate that the proposed system has great potential to aid in detecting and quantifying central obesity in routine clinical evaluations.

Brown Fat Detection and Delineation

The inventors have also presented a novel approach to automatically detect and quantify BATs from PET/CT scans. The proposed structured CCF detects head/neck and thorax regions with accuracies of 97.5% and 90.53%, respectively. In addition, the presented PET-guided BAT co-segmentation algorithm achieved a sensitivity of 92.3%0, and specificity of 82.2%. A new probabilistic distance metric combining Total Variation and Cramer-Von Mises distances for distinguishing BAT from non-BAT regions is also presented.

Organ Detection

The inventors evaluated the transferability of 3D CNN features learned from non-medical datasets onto the medical imaging domain using Geodesic Flow Kernel. The inventors obtained promising results and significant improvement in average precision and organ detection rate. The inventors retrain the 3D CNN on CT data while capturing the contextual relationships between organs within the CNN frame work.

Imaging Modalities

Since PET imaging provides biochemical and physiological activity, it remains the most accepted and preferred modality to study metabolically active BAT regardless of the radiation exposure. It is important to note that most of the BAT examples are obtained from the clinical trials or routine examination of different diseases. Moreover, there are a limited number of clinical trials solely focusing on BAT detection, quantification, and its role in metabolic syndrome, obesity, and other diseases. In order to reduce concerns regarding the ionizing radiation induced by PET/CT, one may consider reducing the radiation exposure of PET/CT scans. There are studies that show that low-dose CT scans have similar tissue HU levels as those in routine CT scans with no diagnostic differences noted, suggesting the use of low(er) dose CT scans in routine examinations. (Ono, K., Hiraoka, T., Ono, A., Komatsu, E., Shigenaga, T., Takaki, H., Maeda, T., Ogusu, H., Yoshida, S., Fukushima, K., et al.: Low-dose CT scan screening for lung cancer: Comparison of images and radiation doses between low-dose CT and follow-up standard diagnostic CT. SpringerPlus 2(1), 1 (2013)). On the other hand, lowering radiation dose in PET equipment is more difficult and expensive than its CT counterpart. (Orenstein, B. W.: Reducing PET Dose. Radiology Today 17(1), 22 (2015); Akin, E. A., Torigian, D. A.: Considerations regarding radiation exposure in performing FDG-PET-CT. Image Wisely (2012)).

Furthermore, the choice of a radiotracer is another concern while reducing the radiation dose. This is because the half-life of the most commonly used tracers is short and the patient size can affect image quality considerably. (Akin 2012). Despite all the financial and logistical disadvantages, lowering the dose in the PET scans is a priority for the manufacturers, radiologists, and nuclear medicine physicians. (Orenstein 2015 and Akin 2012). With low dose PET/CT imaging, the cost-benefit ratio can be significantly improved for studies related to obesity and metabolic syndromes.

Other imaging modalities are also being explored for BAT detection and quantification. The application of MRI, as opposed to CT, in human subjects is promising due to the lack of ionizing radiation and its excellent soft tissue contrast feature. However, current MR sequences do not have high sensitivity and specificity in identifying and quantifying BAT regions. Among a few works considering MR as a potential imaging modality for studying BAT, the use of Multi-point Dixon and multi-echo T2 spin MRI had been explored in mice. (Prakash, K. B., Srour, H., Velan, S. S., Chuang, K. H.: A method for the automatic segmentation of Brown Adipose Tissue. Magnetic Resonance Materials in Physics, Biology and Medicine 29(2), 287-299 (2016)). Fuzzy c-means clustering was used for initial segmentation of BAT followed by a two-layer feed-forward neural network for the separation of BAT from WAT. However, high-field MRI is required for better separation of metabolically active fat regions from the rest and there is no optimal sequence developed yet to do this task. MRI/PET scans may be able to further improve the specificity and sensitivity parameters of the method. Using MRI in the proposed system would allow for personal risk assessment for various metabolic diseases, cancers, cardiovascular diseases and other diseases that may be associated with organ, body region and whole body fat amount. It would also allow for the exploration of tissue, body region and functional quantification of adipose tissue.

Another alternative imaging modality to PET/CT for detection of BAT activation is contrast-enhanced ultrasound (CEUS), a non-invasive and non-ionizing imaging modality. (Flynn, A., Li, Q., Panagia, M., Abdelbaky, A., MacNabb, M., Samir, A., Cypess, A. M., Weyman, A. E., Tawakol, A., Scherrer-Crosbie, M.: Contrast-Enhanced Ultrasound: A Novel Noninvasive, Nonionizing Method for the Detection of Brown Adipose Tissue in Humans. Journal of the American Society of Echocardiography 28(10), 1247-1254 (2015)). As the BAT activation was associated with an increased blood flow to the tissue, it can be measured by assessing the BAT perfusion. CEUS was found to detect increased BAT blood flow during cold exposure relative to warmer conditions. Although the reported experiments were preliminary with evaluations restricted to young and healthy males (mean age, 24.0±2.4 years; mean body mass index, 23.4±3.5 kg/m$^2$), BAT assessment may potentially be performed using CEUS in the future.

It should also be noted that the respiratory motion can be a potential source of error in co-segmentation. It is well known that the respiratory motion can affect PET and CT scans differently due to the possible differences in scan duration. This may induce residual registration mismatch between the two systems and eventually can lead to errors in BAT delineation. In such cases, motion correction algorithms as well as additional deformable registration methods can be employed to minimize registration errors prior to BAT segmentation.

The study has some limitations to be noted. First, when young(er) subjects are scanned with their arms down, muscle may be observed as fat tissue due to photon depletion caused by high bone density. Although the inventors did not observe this issue in the data set presented herein, it may be a pressing issue that must be addressed when generalizing the quantification software into a larger cohort of studies such as clinical trials. Second, the partial volume effect can degrade the detection of small BAT deposits such as paraspinal BAT, particularly when slice thickness in PET is large. Future studies will address these two limitations by integrating partial volume correction and denoising methods into the proposed system. (Xu, Z. et al., Segmentation based denoising of PET images: An iterative approach via regional means and affinity propagation. *International Conference on Medical Image Computing and Computer-Assisted* Intervention, pp. 698-705. (2014); Xu, Z., Bagci, U., Gao, M., Mollura, D. J.: Highly precise partial volume correction for PET images: An iterative approach via shape consistency. In: 2015 IEEE 12th International Symposium on Biomedical Imaging (ISBI). pp. 1196-1199. IEEE (2015)). Inspired by a recent study, another step will be to design a fuzzy object modeling approach for the correction of incorrectly separated muscle and fat tissues due to photon depletion. (Wang, H., Udupa, J. K., Odhner, D., Tong, Y., Zhao, L., Torigian, D. A.: Automatic anatomy recognition in whole-body PET/CT images. Medical Physics 43(1), 613-629 (2016)).

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall there between.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of automatically detecting and quantifying white and brown adipose tissue from an imaging scan of a subject comprising:
providing the imaging scan of the subject wherein the imaging scan is created using computed tomography (CT), positron emission tomography (PET), magnetic resonance imaging (MRI), positron emission tomography/computed tomography (PET/CT), positron emission tomography/magnetic resonance imaging (PET/MRI) or contrast-enhanced ultrasound (CEUS);
automatically detecting a body region of the subject in the imaging scan using extracted convolutional neural network (CNN) features;
segmenting total adipose tissue (TAT) in the body region;
separating and segmenting subcutaneous adipose tissue (SAT) from visceral adipose tissue (VAT) in the body region in the imaging scan of the subject comprising
estimating a SAT-VAT separation boundary;
removing outliers the separation boundary; and
creating a fine SAT-VAT separating surface using three-dimensional (3D) Conditional Random Fields (CRF) using shape, anatomy and appearance cues; and
detecting and segmenting brown adipose tissue (BAT) from other tissue after TAT segmentation in the imaging scan of the subject.

2. The method of claim 1, wherein the body region detected is selected from the group consisting of an abdominal region and a thorax region.

3. The method of claim 2, wherein the body region is automatically detected by using a detection algorithm based on deep learning features.

4. The method of claim 1, wherein the outliers are removed from the boundary using geometric median absolute derivation (MAD) or local outlier scores (LoOS).

5. The method of claim 1, wherein the detecting and segmenting of BAT step further comprises:
performing automatic seed selection for BAT;
delineating potential BAT regions; and
differentiating BAT regions from non-BAT regions.

6. The method of claim 5, wherein fixed Hounsfield unit (HU) interval filtering is used to identify TAT.

7. The method of claim 5, wherein background and foreground seeds are identified during automatic seed selection.

8. The method of claim 5, wherein image co-segmentation using Random Walk (RW) is used to delineate potential BAT regions.

9. The method of claim 5, wherein a probabilistic metric based on a combination of total variation and Cramer-Von Mises distances is used to differentiate BAT regions from non-BAT regions.

10. The method of claim 1, further comprising automatically detecting specific organs comprising:
extracting 3D convolutional neural network (CNN) features from source data;
transforming 3D CNN features from source data to target data by applying Geodesic Flow Kernal (GFK) to the 3D CNN features; and
localizing the organ in a bounding volume using Random Forest;
wherein the target data is organ detection in 3D CT scans.

11. The method of claim 1, wherein the imaging scan is selected from the group consisting of a positron emission tomography/computed tomography (PET/CT) scan, a positron emission tomography/magnetic resonance imaging scan (PET/MRI) and a contrast-enhanced ultrasound (CEUS) scan.

12. A method of creating a risk profile of a subject by automatically detecting and quantifying white and brown adipose tissue from an imaging scan of the subject comprising:
the imaging scan of the subject wherein the imaging scan is created using computed tomography (CT), positron emission tomography (PET), magnetic resonance imaging (MRI), positron emission tomography/computed tomography (PET/CT), positron emission tomography/magnetic resonance imaging (PET/MRI) or contrast-enhanced ultrasound (CEUS);
automatically detecting a body region of the subject in the imaging scan using extracted convolutional neural network (CNN) features wherein the body region detected is an abdominal region or a thorax region;
segmenting total adipose tissue (TAT) in the body region;
separating and segmenting subcutaneous adipose tissue (SAT) from visceral adipose tissue (VAT) in the imaging scan of the subject comprising
estimating a SAT-VAT separation boundary;
removing outliers using geometric median absolute derivation (MAD) or local outlier scores (LoOS); and
creating a fine SAT-VAT separating surface using 3D Conditional Random Fields (CRF) using shape, anatomy and appearance cues;
detecting and segmenting brown adipose tissue (BAT) from other tissue after TAT segmentation in the imaging scan of the subject; and
creating a risk profile based on a quantitative amount of VAT and BAT found in the subject.

13. The method of claim 12, wherein the detecting and segmenting brown adipose tissue (BAT) from other tissue step further comprising:
performing automatic seed selection for BAT;
performing image co-segmentation; and
differentiating BAT regions from non-BAT regions.

14. The method of claim 12, further comprising automatically detecting specific organs comprising:
extracting 3D convolutional neural network (CNN) features from source data;
transforming 3D CNN features from source data to target data by applying Geodesic Flow Kernal (GFK) to the 3D CNN features; and
localizing the organ in a bounding volume using Random Forest;
wherein the target data is organ detection in 3D CT scans.

15. A method of automatically detecting and quantifying white and brown adipose tissue from an imaging scan of a subject comprising:
providing the imaging scan of the subject wherein the imaging scan is created using positron emission tomography/computed tomography (PET/CT);
automatically detecting a body region of the subject in the imaging scan using extracted convolutional neural network (CNN) features;
segmenting total adipose tissue (TAT) in the body region;
separating and segmenting subcutaneous adipose tissue (SAT) from visceral adipose tissue (VAT) in the imaging scan of the subject comprising:
estimating a SAT-VAT separation boundary;
removing outliers using geometric median absolute derivation (MAD) or local outlier scores (LoOS); and creating a fine SAT-VAT separating surface using 3D Conditional Random Fields (CRF) using shape, anatomy and appearance cues;
detecting and segmenting brown adipose tissue (BAT) from other tissue after TAT segmentation in the imaging scan of the subject comprising:
performing automatic seed selection for BAT;
performing image co-segmentation; and
differentiating BAT regions from non-BAT regions.

16. The method of claim 15, further comprising automatically detecting specific organs comprising:
extracting 3D convolutional neural network (CNN) features from source data;
transforming 3D CNN features from source data to target data by applying Geodesic Flow Kernal (GFK) to the 3D CNN features; and
localizing the organ in a bounding volume using Random Forest;
wherein the target data is organ detection in 3D CT scans.

* * * * *